United States Patent
Jaber et al.

(10) Patent No.: US 11,948,687 B2
(45) Date of Patent: Apr. 2, 2024

(54) DEEP LEARNING MODELS FOR REGION-OF-INTEREST DETERMINATION

(71) Applicants: NantOmics, LLC, Culver City, CA (US); NantHealth, Inc., Culver City, CA (US); NantCell, Inc., Culver City, CA (US)

(72) Inventors: Mustafa I. Jaber, Los Angeles, CA (US); Liudmila A. Beziaeva, Culver City, CA (US); Bing Song, La Canada, CA (US); Christopher W. Szeto, Culver City, CA (US); Stephen Charles Benz, Culver City, CA (US); Shahrooz Rabizadeh, Culver City, CA (US)

(73) Assignees: NantCell, Inc., Culver City, CA (US); NantHealth, Inc., Culver City, CA (US); NantOmics, LLC, Culver City, CA (US)

( * ) Notice: Subject to any disclaimer, the term of this patent is extended or adjusted under 35 U.S.C. 154(b) by 412 days.

(21) Appl. No.: 17/381,675

(22) Filed: Jul. 21, 2021

(65) Prior Publication Data

US 2022/0375602 A1  Nov. 24, 2022

Related U.S. Application Data

(60) Provisional application No. 63/192,508, filed on May 24, 2021.

(51) Int. Cl.
*G16H 50/20* (2018.01)
*G06N 3/08* (2023.01)
(Continued)

(52) U.S. Cl.
CPC .............. *G16H 50/20* (2018.01); *G06N 3/08* (2013.01); *G06T 7/0012* (2013.01); *G06T 7/11* (2017.01); *G06T 2207/30096* (2013.01)

(58) Field of Classification Search
CPC ........ G06N 20/20; G06N 3/0464; G06N 3/08; G06N 3/0895; G06N 5/01;
(Continued)

(56) References Cited

U.S. PATENT DOCUMENTS 10,229,342 B2  3/2019  Song et al.
10,346,712 B2  7/2019  Siddiqui
(Continued)

OTHER PUBLICATIONS

Yan Xu , "Large scale tissue histopathology image classification, segmentation, and visualization via deep convolutional activation features," May 26, 2017, BMC Bioinformatics (2017) 18:281,pp. 1-15.*

(Continued)

*Primary Examiner* — Omar S Ismail
(74) *Attorney, Agent, or Firm* — Harness Dickey & Pierce P.L.C.

(57) ABSTRACT

A method of determining a region of interest in an image of tissue of an individual by an apparatus including processing circuitry may include executing, by the processing circuitry, instructions that cause the apparatus to partition an image of tissue of an individual into a set of areas, identify a tissue type of each area of the image, and apply a classifier to the image to determine a region of interest, the classifier being configured to determine regions of interest based on the tissue types of the set of areas of the image.

30 Claims, 19 Drawing Sheets

(51) Int. Cl.
*G06T 7/00* (2017.01)
*G06T 7/11* (2017.01)

(58) Field of Classification Search
CPC . G06T 2207/10056; G06T 2207/20021; G06T 2207/20084; G06T 2207/30024; G06T 2207/30096; G06T 7/0012; G06T 7/11; G06V 10/25; G06V 10/454; G06V 2201/03; G16H 30/40; G16H 50/20
See application file for complete search history.

(56) References Cited

U.S. PATENT DOCUMENTS

| | | | |
|---|---|---|---|
| 10,607,343 B2 | 3/2020 | Song et al. | |
| 10,769,788 B2 | 9/2020 | Song et al. | |
| 10,796,196 B2 | 10/2020 | Song et al. | |
| 2003/0215120 A1* | 11/2003 | Uppaluri | A61B 6/505 382/128 |
| 2004/0218794 A1* | 11/2004 | Kao | G06T 7/143 382/128 |
| 2011/0182490 A1* | 7/2011 | Hoyt | G06V 20/698 382/128 |
| 2016/0253466 A1* | 9/2016 | Agaian | G06N 5/043 382/128 |
| 2020/0226422 A1* | 7/2020 | Li | G06N 3/04 |
| 2020/0272864 A1* | 8/2020 | Faust | G06V 10/764 |
| 2020/0294659 A1* | 9/2020 | Gopinath | A61B 90/37 |
| 2020/0388029 A1* | 12/2020 | Saltz | G06V 10/267 |
| 2021/0256699 A1* | 8/2021 | Wainrib | G06T 7/0012 |

OTHER PUBLICATIONS

Naofumi Tomita,"Attention-Based Deep Neural Networks for Detection of Cancerous and Precancerous Esophagus Tissue on Histopathological Slides,"Nov. 6, 2019,JAMA Network Open. 2019;2(11),pp. 1-9.*

Brendon Lutnick,"Iterative annotation to ease neural network training: Specialized machine learning in medical image analysis," Dec. 18, 2018, Image and Video Processing,arXiv:1812.07509,Nature Machine Intelligence 1.2 (2019): 112,pp. 4-7.*

Simon Graham,"Hover-Net: Simultaneous segmentation and classification of nuclei in multi-tissue histology images,"Sep. 18, 2019,Medical Image Analysis 58 (2019) 101563, pp. 1-10.*

Caner Mercan,"Deep Feature Representations for Variable-Sized Regions of Interest in Breast Histopathology,"Jun. 4, 2021,IEEE Journal of Biomedical and Health Informatics, vol. 25, No. 6, Jun. 2021,pp. 2041-2048.*

Javad Noorbakhsh,"Deep learning-based cross-classifications reveal conserved spatial behaviors within tumor histological images," Dec. 11, 2020, Nature Communications(2020),pp. 1-10.*

Raluca Brehar,"Comparison of Deep-Learning and Conventional Machine-Learning Methods for the Automatic Recognition of the Hepatocellular Carcinoma Areas from Ultrasound Images," May 29, 2020,Sensors 2020,20,3085, pp. 1-19.*

Lutnick, B., et al., "An integrated iterative annotation technique for easing neural network training in medical image analysis," Natl Mach Intell., 1(2): 112-119 (2019).

Bankhead, P., et al., "QuPath: Open source software for digital pathology image analysis," Scientific Reports, 7(16878): 1-7 (2017).

Jaber, M.I., et al., "Deep-learning image-based tumor, stroma, and lymphocytes spatial relationships and clinical features that affect survival in pancreatic cancer patients," AACR Virtual Special Conference on Pancreatic Cancer, Sep. 29-30, 2020.

Jaber, M.I., et al., "Deep-learning image-based features stratify risk in HER2-breast cancer patients," AACR Virtual Annual Meeting, Apr. 10-15 and May 17-21, 2021.

Jaber, M.I., et al., "Tumor-infiltrating lymphocytes (TILs) found elevated in lung adenocarcinomas (LUAD) using automated digital pathology masks derived from deep-learning models," Sixth AACR-IASLC International Joint Conference, Jan. 11-14, 2020.

* cited by examiner

| Low risk | f4 = percent of lymphocytes within 200um from tumor | f7 = percent of stroma within 100um from tumor | f3 = percent of lymphocytes within 100um from tumor | f2 = percent of tissue that is lymphocytes |
|---|---|---|---|---|
| TCGA-HZ-A8P1-01Z-00-DX1 | 45.4545 | 2.1668 | 9.0909 | 0.4604 |
| TCGA-F2-A7TX-01Z-00-DX1 | 96.6265 | 38.6619 | 69.4284 | 16.2899 |
| TCGA-OE-A75W-01Z-00-DX1 | 83.7061 | 16.8822 | 46.4058 | 8.3184 |

| High risk | f4 = percent of lymphocytes within 200um from tumor | f7 = percent of stroma within 100um from tumor | f3 = percent of lymphocytes within 100um from tumor | f2 = percent of tissue that is lymphocytes |
|---|---|---|---|---|
| TCGA-3A-A9IZ-01Z-00-DX1 | 53.1876 | 12.1540 | 17.1828 | 8.1839 |
| TCGA-IB-A5SO-01Z-00-DX1 | 54.3373 | 5.2897 | 18.1928 | 3.5219 |

FIG. 5

| TCGA Cancer Cohort | WSI | Total patch count | Accuracy |
|---|---|---|---|
| TCGA-BRCA Breast | TCGA-GM-A2DF-01Z-00-DX1 | 18,653 | 0.94 |
| TCGA-BLCA Bladder | TCGA-XF-A9SL-01Z-00-DX1 | 24,485 | 0.98 |
| TCGA-KIRP Kidney | TCGA-A4-7734-01Z-00-DX1 | 5,053 | 0.95 |
| TCGA-KIRC Kidney | TCGA-B0-4706-01Z-00-DX1 | 32,983 | 0.95 |
| TCGA-LUSC Lung | TCGA-39-5022-01Z-00-DX1 | 16,523 | 0.92 |
| TCGA-PRAD Prostate | TCGA-HC-7075-01Z-00-DX1 | 2,368 | 0.89 |

| TCGA Cancer Cohort | WSI | Total patch count | Accuracy |
|---|---|---|---|
| TCGA-LUAD Lung | TCGA-55-7913-01Z-00-DX1 | 1,957 | 0.93 |
| TCGA-COAD Colon | TCGA-G4-6626-01Z-00-DX1 | 16,092 | 0.92 |
| TCGA-STAD Stomach | TCGA-VQ-A923-01Z-00-DX1 | 22,039 | 0.80 |
| TCGA-PAAD Pancreas | TCGA-HZ-7920-01Z-00-DX1 | 6,021 | 0.82 |
| TCGA-CESC Cervical | TCGA-LP-A5U3-01Z-00-DX1 | 21,699 | 0.94 |
| TCGA-READ Rectum | TCGA-DY-A1DC-01Z-00-DX1 | 20,573 | 0.88 |

FIG. 12B

| TCGA Cancer Cohort | WSI | Total patch count | Accuracy |
|---|---|---|---|
| TCGA-ESCA Esophageal | TCGA-V5-A7RC-01Z-00-DX1 | 26,984 | 0.92 |
| TCGA-HNSC Head and Neck | TCGA-CN-5360-01Z-00-DX1 | 10,591 | 0.87 |
| TCGA-OV Ovarian | TCGA-57-1585-01Z-00-DX1 | 20,573 | 0.80 |
| TCGA-THCA Thyroid | TCGA-EM-A2CP-01Z-00-DX1 | 4,061 | 0.90 |
| TCGA-LIHC Liver | TCGA-DD-AAE6-01Z-00-DX1 | 25,493 | 0.98 |
| TCGA-UCEC Uterine | TCGA-BS-A0V8-01Z-00-DX1 | 33,511 | 0.80 |

FIG. 12C

DEEP LEARNING MODELS FOR REGION-OF-INTEREST DETERMINATION

CROSS-REFERENCE TO RELATED APPLICATIONS

This application claims the benefit of U.S. Provisional Application No. 63/192,508 filed May 24, 2021, the entire disclosure of which is incorporated by reference.

FIELD

The present disclosure relates to the field of digital image analysis using machine learning models, and more particularly to determining regions of interest in a digital image of tissue of an individual using deep learning models.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

In the field of medicine, many scenarios involve an analysis of a region of interest in an digital image of tissue of an individual. For example, analysis of an image of a cancer tumor may enable a determination of a tumor class based on characteristics such as location, size, shape, symmetry, and composition. The analysis may further enable a diagnosis of an individual, a recommendation of a treatment such as a medication regimen, or a prediction of a prognosis of the individual, such as a survivability prediction. For example, analysis of an image of a cancer tumor may enable predictions such as tumor behavior or aggressiveness, the probability and rate of growth and/or metastasis, a likely survival rate. The analysis may further guide decisions about medical treatment, such as a selection, type, and/or timing of chemotherapy, surgery, and palliative care.

Techniques for evaluating an image of a region of interest may utilize one or more computer-based machine learning models. For example, a training data set of tumor samples with known properties, such as data about the tumor, the individual from whom the tumor were removed, and/or the clinical value (such as the prognosis) for the individual, may be generated. A machine learning classifier may be trained using the training data set with labels that indicate the classes represented by each input, such as whether each tumor represents a high-risk tumor with a poor prognosis or a low-risk tumor with a good prognosis. The training process may result in a trained machine learning classifier that classifies new input in a manner that is consistent with the examples of the training data set.

A variety of different machine learning models may be selected as classifiers for regions of interest, such as Bayesian classifiers, artificial neural networks, and support vector machines (SVMs). As a first such example, a convolutional neural network (CNN) may process an n-dimensional input to detect features of images of tumors that may occur therein. A feature vector, such as a pixel array of an image of a tumor, may be provided to a convolutional neural network including a sequence of convolutional layers of neurons. Each convolutional layer may produce a feature map indicating some image features of the tumor that were detected at a level of detail, which may be processed by a next convolutional layer in the sequence. The feature map produced by the final convolutional layer of the convolutional neural network may be processed by a classifier of the tumor, which may be trained to indicate whether the feature map is similar to the feature maps of objects in the images of the training data set. For example, the CNN may be trained to determine visual features of a tumor that are correlated with high-risk and low-risk prognoses. However, analysis of the visual features of a tumor may be difficult, for example, due to variance among the visual features that may be associated with different tumor types, and/or the relationship between the tumor and other types of tissue in the image, such as the location of the tumor relative to other anatomic features of the individual.

SUMMARY

In some example embodiments, an apparatus may include processing circuitry configured to partition an image of tissue of an individual into a set of areas, identify a tissue type of each area of the image, and apply a classifier to the image to determine a region of interest, the classifier being configured to determine regions of interest based on the tissue types of the set of areas of the image.

In some example embodiments, a system may include an image evaluator configured to partition an image of tissue of an individual into a set of areas, a first classifier configured to identify a tissue type of each area of the image, and a second classifier configured to determine a region of interest in the image, the second classifier being configured to determine regions of interest based on the tissue types of the set of areas of the image.

In some example embodiments, a non-transitory computer-readable storage medium storing instructions that, when executed by processing circuitry, cause an apparatus to partition an image of tissue of an individual into a set of areas, identify a tissue type of each area of the image, and apply a classifier to the image to determine a region of interest, the classifier being configured to determine regions of interest based on the tissue types of the set of areas of the image.

In some example embodiments, a method of operating an apparatus may include processing circuitry, the method including executing, by the processing circuitry, instructions that cause the apparatus to partition an image of tissue of an individual into a set of areas, identify a tissue type of each area of the image, and apply a classifier to the image to determine a region of interest, the classifier being configured to determine regions of interest based on the tissue types of the set of areas of the image.

In some example embodiments, the classifier is a convolutional neural network including a convolutional classification layer that has been trained to determine regions of interest in images based on the tissue types of the set of areas of the image.

Some example embodiments may include storing a description of the region of interest based on the tissue types of the set of areas, wherein the classifier is further configured to determine the region of interest by matching the description of the region of interest with the tissue types of the set of areas. In some example embodiments, the description of the region of interest may include one or more of: a number of a subset of areas of a tissue type, a size of a subset of areas of a tissue type, a density of a subset of areas of a tissue type, a moment of a subset of areas of a tissue type, a shape of a subset of areas of a tissue type, a symmetry of a subset of areas of a tissue type, a spatial distribution of a subset of areas of a tissue type, a visual appearance of a subset of areas of a tissue type, or a distance between a subset of areas of a first tissue type and a subset of areas of a second tissue type. Some example embodiments may include determining a similarity measurement between the region of interest in the image and the region of interest of the description.

Some example embodiments may include generating the description based on a training data set of images of regions of interest. Some example embodiments may include determining at least one area of at least one image of the training data set that does not match the description, and requesting an identification of the tissue type of the at least one area of the at least one image. Some example embodiments may include, based on receiving the identification of the tissue type, updating the description based on the identification. In some example embodiments, generating the description may include receiving, from a user, an indication of a region of interest in one or more of the images of the training data set, and generating the description based on features of the one or more images of the training data set and the indication received from the user. In some example embodiments, generating the description may include partitioning an image of the training data set into a set of areas, determining the areas of the image of the training data set that are within the region of interest indicated by the user, and determining at least one visual feature of the areas of the image of the training data set that are within the region of interest indicated by the user.

In some example embodiments, storing the description may further include storing a first description of a tissue type of a first region type, and storing a second description of a tissue type of a second region type that is different than the first region type; and the classifier may be further configured to, determine a first region of interest in the image by matching the set of areas of the image with the first description of the first region type, and determine a second region of interest in the image by matching the set of areas of the image with the second description of the second region type. In some example embodiments, the first description describes a cancerous tissue region type, and the second description describes a noncancerous tissue region type. In some example embodiments, the first description describes a first cancer region type, and the second description describes a second cancer region type that is different than the first cancer region type. Some example embodiments may include determining that a similarity measurement between the region of interest in the image and regions of interest of the first description is greater than a similarity measurement between the region of interest in the image and regions of interest of the second description.

Some example embodiments may include generating at least one mask indicating the areas of one tissue type among the set of areas, and presenting the image including the at least one mask. In some example embodiments, presenting the image may include one or both of: presenting a first mask of a first tissue type with a first indicator, or presenting a second mask of a second tissue type with a second visual indicator that is different than the first visual indicator. Some example embodiments may include presenting the image with an indicator of the set of areas of the image that are determined as the region of interest. Some example embodiments may include storing a mask indicating a labeled region of interest, and presenting the image may include presenting an indicator of the labeled region of interest. Some example embodiments may include generating at least one measurement of the region of interest based on at least one visual feature of the set of areas of the region of interest.

In some example embodiments, the at least one measurement may include one or more of: a size of the region of interest, a shape of the region of interest, a symmetry of the region of interest, a color of the region of interest, a density of the region of interest, or a moment of the region of interest.

Some example embodiments may include determining a spatial relationship between areas of a first tissue type and areas of a second tissue type, and presenting the image with an indicator of the spatial relationship. In some example embodiments, the spatial relationship may include one or more of: a union between the areas of the first tissue type and the areas of the second tissue type, an intersection between the areas of the first tissue type and the areas of the second tissue type, a complement between the areas of the first tissue type and the areas of the second tissue type, or a distance between the areas of the first tissue type and the areas of the second tissue type. Some example embodiments may include determining a measurement of the spatial relationship between the areas of the first tissue type and the areas of the second tissue type.

Some example embodiments may include determining one or more of: a diagnosis of the individual based on the region of interest, a prognosis of the individual based on the region of interest, or a treatment of the individual based on the region of interest.

BRIEF DESCRIPTION OF THE DRAWINGS

The present disclosure will become more fully understood from the detailed description and the accompanying drawings. In the drawings, reference numbers may be reused to identify similar and/or identical elements.

FIG. 5 is an illustration of a classification of tumors of different classes based on a feature subset in accordance with some example embodiments.

FIG. 12A is a comparative illustration of a first set of labeled images and experimental results of using a classifier to determine a region of interest in accordance with the techniques presented herein.

FIG. 12B is an illustration of a second set of labeled images and experimental results of using a classifier to determine a region of interest in accordance with the techniques presented herein.

FIG. 12C is an illustration of a third set of labeled images and experimental results of using a classifier to determine a region of interest in accordance with the techniques presented herein.

DETAILED DESCRIPTION

A. Introduction

The following introduction is intended to provide an overview of some machine learning features that relate to some example embodiments. One should appreciate the following discussion relates to processing digital images through execution of one or more software instruction sets or suits on one or more processor.

Figure 1:
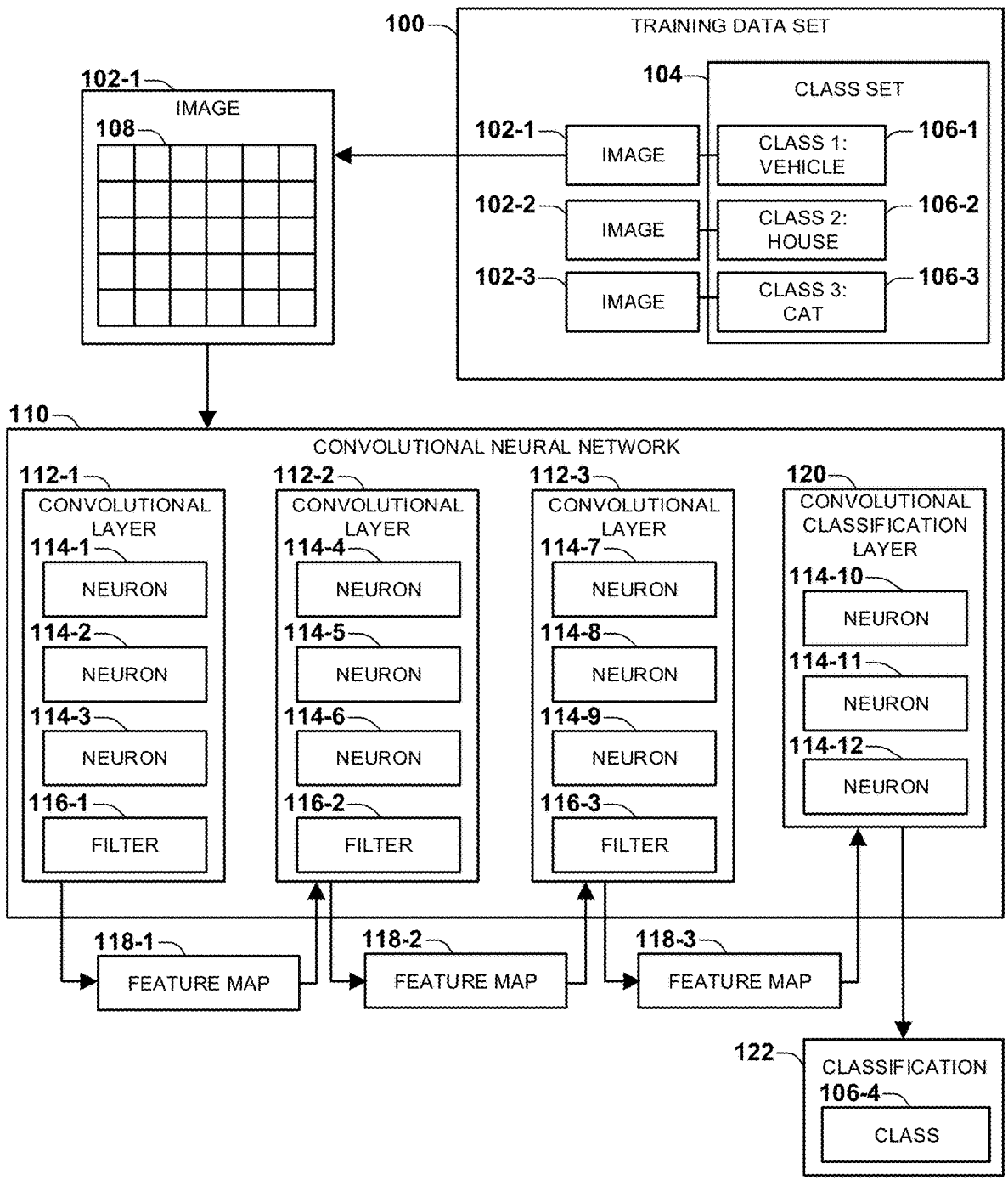
FIG. 1 is an illustration of an example convolutional neural network.

FIG. 1 is an example of a convolutional neural network (CNN) 110 that is trained to process an n-dimensional input to detect a number of features.

In the example of FIG. 1, the convolutional network 110 processes images 102 as a two-dimensional array of pixels 108 in one or more colors, but some such convolutional neural networks 110 may process other forms of data, such as sound, text, or a signal from a sensor possibly having other data modalities.

In the example of FIG. 1, a training data set 100 is provided as a set of images 102 that are each associated with a class 106 from a class set 104. For example, the training data set 100 may include a first image 102-1 of a vehicle that is associated with a first class 106-1 for images of vehicles; a second image 102-2 of a house that is associated with a second class 106-2 for images of houses; and a third image 102-3 of a cat that is associated with a third class 106-3 for images of cats. The associations of the images 102 with the corresponding classes 106 are sometimes known as labels of the training data set 100.

As further shown in FIG. 1, each image 102 may be processed by a convolutional neural network 110 that is organized as a series of convolutional layers 112, each having a set of neurons 114 and one or more convolutional filters 116. In the first convolutional layer 112-1, each neuron 114 may apply a first convolutional filter 116-1 to a region of the image, and may output an activation that indicates whether the pixels in the region corresponds to the first convolutional filter 116-1. The collection of activations produced by the neurons 114 of the first convolutional layer 112-1, known as a feature map 118-1, may be received as input by a second convolutional layer 112-2 in the sequence of convolutional layers 112 of the convolutional neural network 110, and the neurons 114 of the second convolutional layer 112-2 may apply a second convolutional filter 116-2 to the feature map 118-1 produced by the first convolutional layer 112-1 to produce a second feature map 118-2. Similarly, the second feature map 118-2 may be received as input by a third convolutional layer 112-3, and the neurons 114 of the third convolutional layer 112-3 may apply a third convolutional filter 116-3 to the feature map 118-2 produced by the second convolutional layer 112-2 to produce a third feature map 118-3. Such machine learning models that include a significant plurality of layers or more complex architectures of layers are sometimes referred to as deep learning models.

As further shown in FIG. 1, the third feature map 118-3 produced by the third and final convolutional layer 112-3 may be received by a convolutional classification layer 120, such as a "dense" or fully-connected layer, which may perform a classification of the third feature map 118-3 to determine a classification of the content of the image 102-1. For example, each neuron 114 of the convolutional classification layer 120 may apply a weight to each activation of the third feature map 118-3. Each neuron 114 outputs an activation that is a sum of the products of each activation of the third feature map and the weight connecting the neuron 114 with the activation. As a result, each neuron 114 outputs an activation that indicates the degree to which the activations included in the third feature map 118-3 match the corresponding weights of the neuron 114. Further, the weights of each neuron 114 are selected based on the activations of third feature maps 118-3 that are produced by the images 102 of one class 106 of the class set 104. That is, each neuron 114 outputs an activation based on a similarity of the third feature map 118-3 for a currently processed image 102-1 to the third feature maps 118-3 that are produced by the convolutional neural network 110 for the images 102 of one class 106 of the class set 104. A comparison of the output of the neurons 114 of the convolutional classification layer 120 may permit the convolutional neural network 110 to perform a classification 122 by choosing the class 106-4 with the highest probability of corresponding to the third feature map 118-3. In this manner, the convolutional neural network 110 may perform a classification 122 of the image 102-1 as the class 106 of images 102 that most closely resemble the image 102.

As further shown in FIG. 1, a training process may be applied to train the convolutional neural network 110 to recognize a class set 104 that is represented by a particular set of images 102 of a training data set 100. During the training process, each image 102 of the training data set 100 may be processed by the convolutional neural network 110, resulting in a classification 122 of the image 102. If the classification 122 is incorrect, the convolutional neural network 110 may be updated by adjusting the weights of the neurons 114 of the convolutional classification layer 120 and the filters 116 of the convolutional layers 112 such that the classification 122 of the convolutional neural network 110 is closer to the correct classification 122 for the image 102 being processed. Repeatedly training the convolutional neural network 110 on the training data set 100, while incrementally adjusting the convolutional neural network 110 to produce a correct classification 122 for each image 102, may result in convergence of the convolutional neural network 110, wherein the convolutional neural network 110 correctly classifies the images 102 of the training data set 100 within an acceptable range of error. Examples of convolutional neural network architectures include ResNet and Inception.

As discussed with respect to FIG. 1, machine learning models such as convolutional neural networks 110 may be capable of classifying inputs, such as images 102, based on an arrangement of features with respect to one another, such as a characteristic number, orientation, and positioning of recognizable features. For example, a convolutional neural network 110 may classify an image 102 by producing a first feature map 118-1 indicating the detection of certain geometric shapes, such as curves and lines, that occur in various locations within the image 102; a second feature map 118-2 indicating that the geometric shapes are arranged to produce certain higher-level features, such as a set of curves arranged as a circle or a set of lines arranged as a rectangle; and a third feature map 118-3 indicating that the higher-level features are arranged to produce even higher-level features, such as a set of circles arranged as a wheel and a set of rectangles arranged as a door frame. A neuron 114 of the convolutional classification layer 120 of the convolutional neural network 110 may determine that the features of the third feature map 118-3 (such as two wheels positioned between two door frames) are arranged in such a manner as to depict the side of a vehicle such as a car. Similar classification 122 may occur by other neurons 114 of the convolutional classification layer 120 to classify images 102 as belonging to other classes 106 of the class set 104, such as an arrangement of two eyes, two triangular ears, and a nose that depicts a cat, or an arrangement of windows, a door frame, and a roof that depicts a house. In this manner, machine learning models such as convolutional neural networks may classify inputs (such as images 102) based upon an arrangement of features that correspond to similar arrangements of features as depicted in the inputs (such as images 102) of a training data set 100. Additional details about convolutional neural networks and other machine learning models, including support vector machines, may be found in U.S. Patent Application 62/959,931 (PCT/US2021/012980), which is incorporated by reference as if fully rewritten herein.

B. Distribution-Based Identification of Tissue Types

In some machine learning scenarios, a classification of an input (such as an image) may occur based on an arrangement of recognizable features with respect to one another, such as a number, orientation, and/or positioning of recognizable patterns of pixels as detected in a feature map 118 of a convolutional neural network 110. However, in some other scenarios, the classification may not be based on an arrangement of features with respect to one another, but instead based on a distribution of features in the input, such as whether a density variance of a feature over the area of the input correspond to a recognizable density variation that is characteristic of a class 106. That is, the classes 106 of a class set 104 might not be recognizable as a set of lower-level features corresponds to a recognized arrangement (number, orientation, and/or positioning, etc.) of higher-level features with respect to one another that corresponds to a class 106. Instead, each class 106 may be recognizable as a correspondence of the distribution of the activation of a feature with some properties of the input. Such distribution may not reflect any particular number, orientation, and/or positioning of the activations of features of the input, but, rather, may indicate whether the distribution of the activation of the feature corresponds to the distribution of the activation of the feature for respective classes 106. In such scenarios, the inputs of each class 106 (such as a training data set) may be associated with a characteristic distribution of the activation of the feature, and a classification of an input may be based upon whether the distribution of the activation of the feature of the input corresponds to the distribution of the activation of the feature among the inputs of each class 106. Such distribution-based classification may also arise in a variety of scenarios.

Figure 2A:
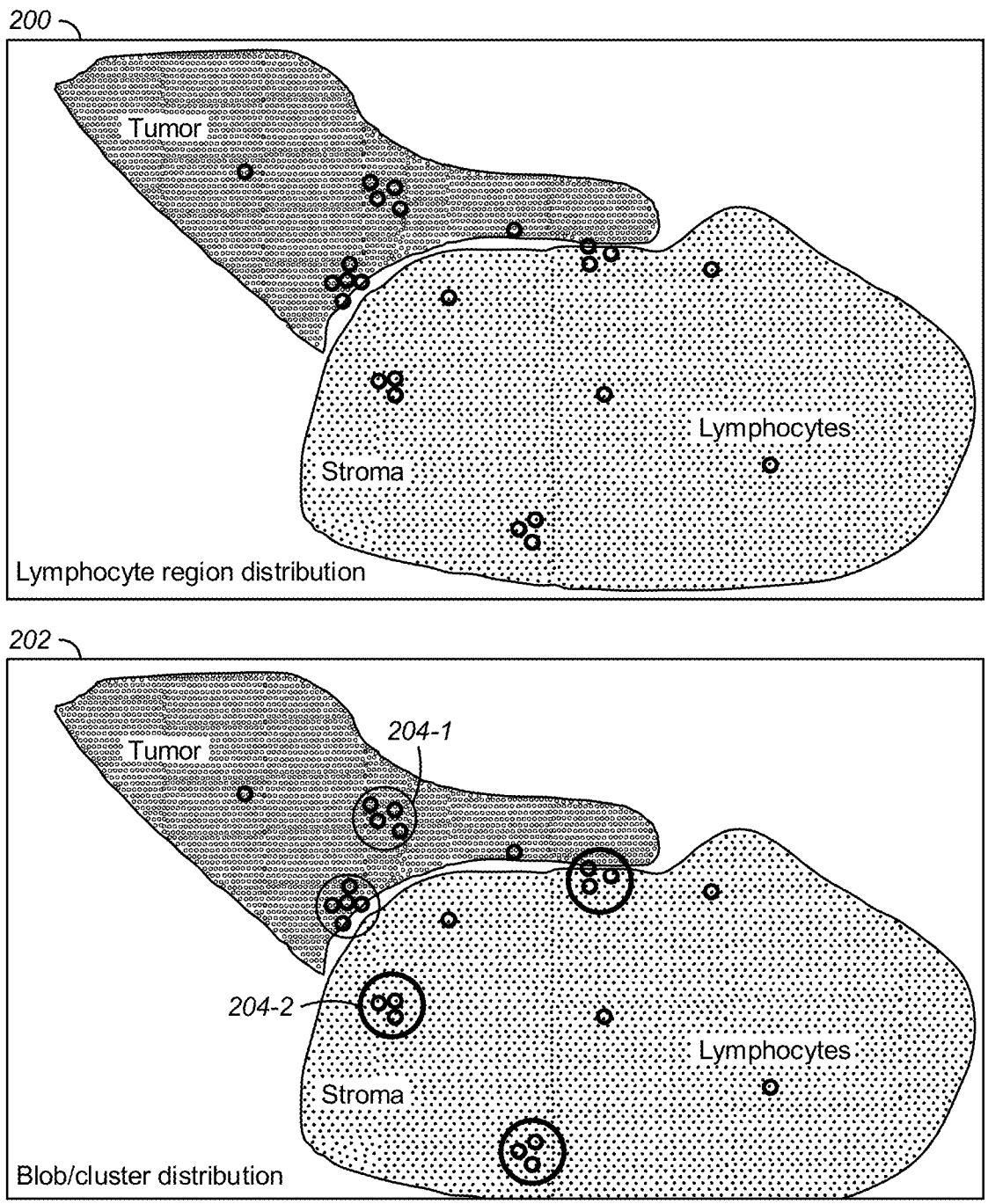
FIG. 2A is an illustration of an example image analysis to identify area types and distributions of lymphocytes in an image of a tumor in accordance with some example embodiments.
Figure 2B:
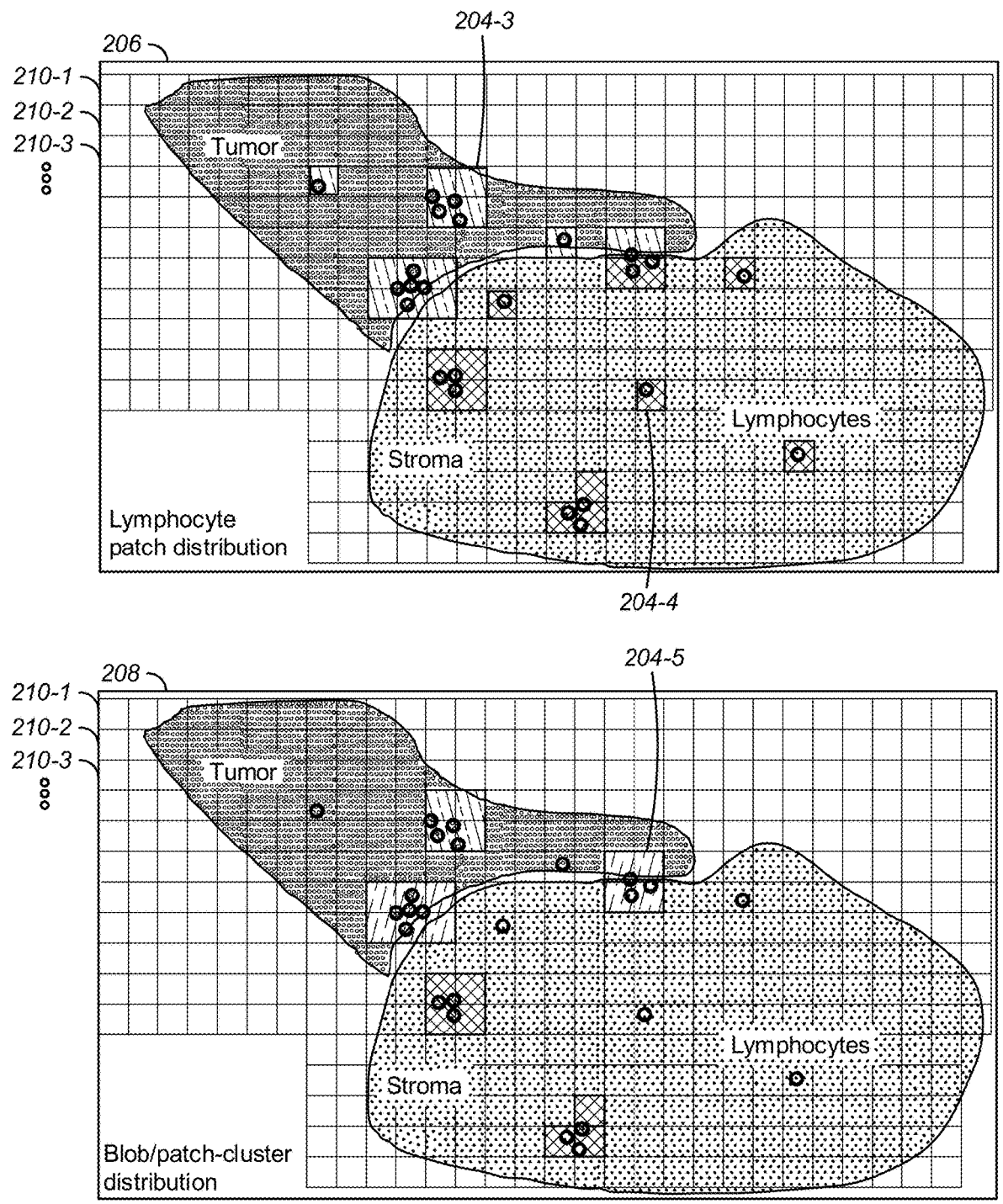
FIG. 2B is an illustration of an example image analysis to classify the distribution of lymphocytes in an image of a tumor in accordance with some example embodiments.

FIGS. 2A and 2B together show an example of several types of image analysis that may be used to identify area types and distributions of lymphocytes in an image of a tumor in some example embodiments.

FIG. 2A is an illustration of an example image analysis to identify area types and distributions of lymphocytes in an image of a tumor in accordance with some example embodiments. As shown in FIG. 2A, a data set may include an image 102 of tissue of an individual with a type of tumor, as well as stroma that includes connective tissue and support for the tumor. Classification of the features of the image 102 may enable an identification of areas, for example, portions of the image 102 that have areas with similar features. A further identification of areas of the feature map 118 that include a certain feature of a filter 116 may enable a determination 200 of area types of the respective areas, such as a first area the image 102 that depicts a tumor, and a second area of the image 102 that depicts stroma. Each filter 116 of the convolutional neural network 110 may therefore be regarded as a mask that indicates the areas of the image 102 of a particular area type, such as the presence, size, shape, symmetry, and/or extent of a tumor, or of stroma that is adjacent to a tumor.

Further, the image 102 may show the presence of lymphocytes, which may be distributed with regard to the tumor, stroma, and other tissue. Further analysis of the image may enable a determination 202 of lymphocyte clusters 204 as contiguous areas and/or as areas in which a concentration of lymphocytes is high (for example, compared with the concentration of lymphocytes in other parts of the image, or with a concentration threshold), for example, by counting the number of lymphocytes present within a particular area of the image 102. Thus, the lowest convolutional layers 112 and filters 116 of a convolutional neural network 110 may be capable of identifying features that are indicative of tumor, stroma, and lymphocytes.

FIG. 2B is an illustration of an example image analyses to classify the distribution of lymphocytes in an image of a tumor in accordance with some example embodiments. In FIG. 2B, a first image analysis 206 may be performed by first partitioning the image 102 into a set of areas, and classifying each area of the image 102 as tumor, tumor-adjacent, stroma, stroma-adjacent, or elsewhere. As a result, each area that includes a lymphocyte cluster 204 may further characterize the lymphocyte cluster 204 based on the area type, for example, a first lymphocyte cluster 204-3 that occurs within a tumor and a second lymphocyte cluster 204-4 that occurs within stroma.

A second image analysis 208 may be performed to further compare the locations of lymphocyte clusters 204 with the locations of different area types to further characterize the lymphocyte clusters 204. For example, the first lymphocyte cluster 204-3 may be determined to occur within a central part of a tumor area, and/or within a first threshold distance of a location identified as a center of mass of the tumor, and may therefore be characterized as a tumor-infiltrating lymphocyte (TIL) cluster. Similarly, the second lymphocyte cluster 204-4 may be determined to occur within a central part of a stroma area, and therefore representing a stroma-infiltrating lymphocyte cluster. However, a third cluster 204-5 may be determined to occur within a peripheral part of a tumor area, and/or within a second threshold distance of the tumor (the second threshold distance being larger than the first threshold distance), and may therefore be characterized as a tumor-adjacent lymphocyte cluster. Alternatively or additionally, the third cluster 204-5 may be determined to occur within a peripheral part of a stroma area, and/or within a second threshold distance of the stroma (the second threshold distance being larger than the first threshold distance), and may therefore be characterized as a stroma-adjacent lymphocyte cluster. Some example embodiments may classify the area as tumor, stroma, or lymphocytes; with two labels, such as tumor and lymphocytes, stroma and lymphocytes, or tumor and stroma; and/or with three labels, such as tumor, stroma, and lymphocytes. Some example embodiments may then be configured to identify clusters 204 of lymphocytes that appear in each area of the image 102, and to tabulate the areas to determine the distribution. In this manner, the image analysis of the image 102, including the feature maps 118 provided by different filters 116 of the convolutional neural network 110, may be used to determine and characterize the distribution and/or concentration of lymphocyte sin the image of the tumor in some example embodiments.

Figure 3:
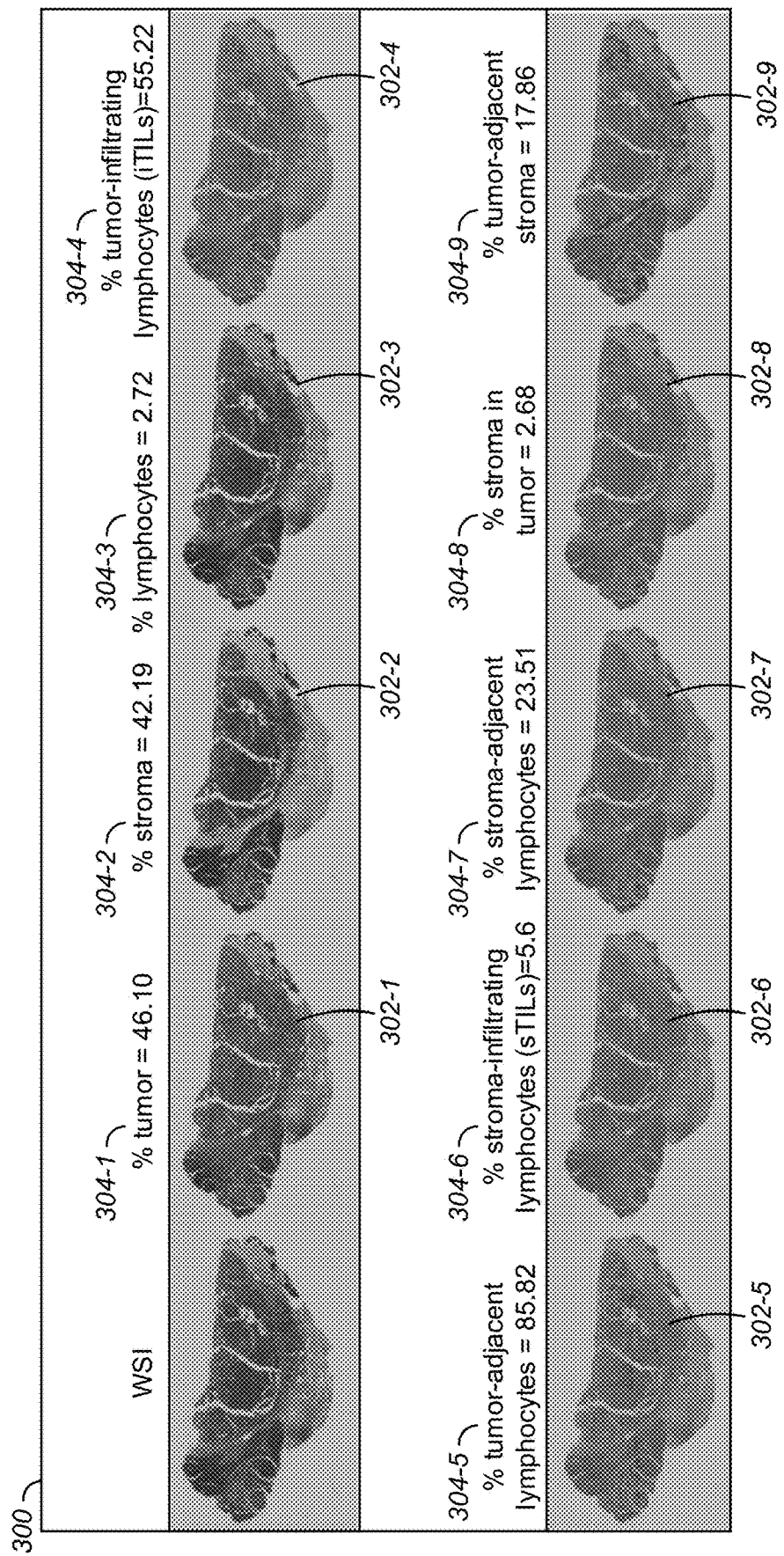
FIG. 3 is an illustration of a set of masks of lung tissue samples including a lymphocyte distribution of lymphocytes by an example machine learning model in accordance with some example embodiments.

FIG. 3 is an illustration of a mask set 300 of masks 302 of real-world lung tissue samples including a lymphocyte distribution of lymphocytes by an example machine learning model in accordance with some example embodiments.

As shown in FIG. 3, masks 302 of the image 102 may be prepared, each mask 302 indicating the area of the image 102 that correspond to one or more area types. For example, a first mask 302-1 may indicate areas of the image 102 that are identified as tumor areas. A second mask 302-2 may indicate areas of the image 102 that are identified as stroma areas. A third mask 302-3 may indicate areas of the image 102 that are identified as lymphocyte areas. Still further masks may be characterized based on the distribution of the features in the feature maps 118. For example, a fourth mask 302-4 may indicate areas of the image 102 that are identified as tumor-infiltrating lymphocyte areas. A fifth mask 302-5 may indicate areas of the image 102 that are identified as tumor-adjacent lymphocyte areas. A sixth mask 302-6 may indicate areas of the image 102 that are identified as stroma-infiltrating lymphocytes areas. A seventh mask 302-7 may indicate areas of the image 102 that are identified as stroma-adjacent lymphocytes areas. An eighth mask 302-8 may indicate areas of the image 102 that are identified as overlapping stroma areas and tumor areas. A ninth mask 302-9 may indicate areas of the image 102 that are identified as tumor-adjacent stroma areas.

In some example embodiments, the image 102 may also be processed to determine a variety of measurements 304 of the respective area types of the image 102. For example, a concentration of each area type, as a percentage of the image 102, may be calculated (e.g., the number of pixels 108 corresponding to each area as compared with the total number of pixels of the image 102, optionally taking into account an apparent concentration of the features, such as a density or count of lymphocytes in respective areas of the image 102). In this manner, the image analysis of the image 102 based on the distribution analysis shown in FIGS. 2A and 2B may be aggregated as a mask set 300 of masks 302 and/or quantities in some example embodiments.

Figure 4:
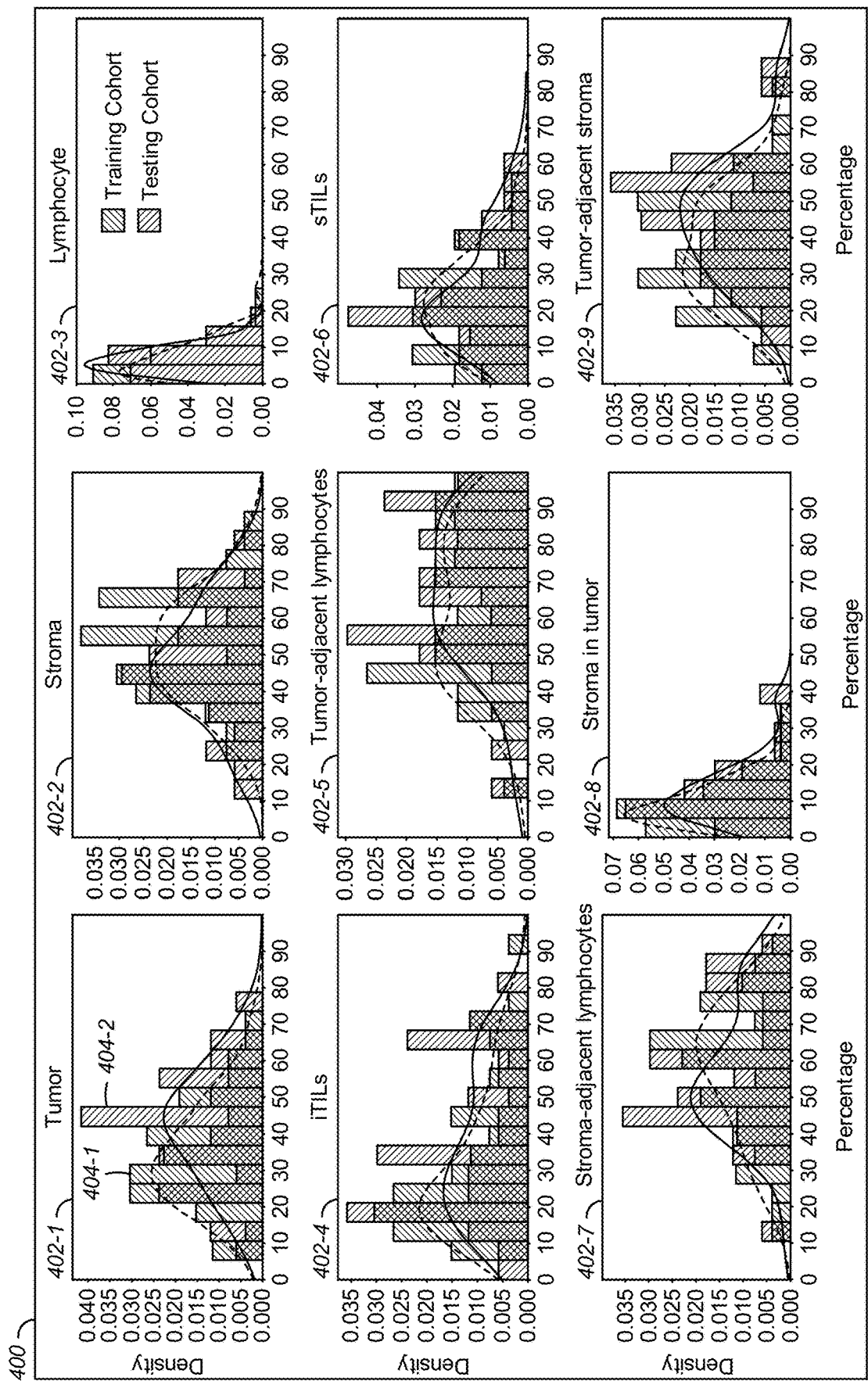
FIG. 4 is an illustration of an example machine learning model that classifies tumors in accordance with some example embodiments.

FIG. 4 is an illustration of a characterization 400 of a set of images of pancreatic adenocarcinoma tissue samples in accordance with some example embodiments.

In the charts of FIG. 4, a set of tumors is characterized by the system shown in FIGS. 2A and 2B to determine a distribution of the detected features of tumor, such as tumor areas 402-1, stroma areas 402-2, lymphocyte areas 402-3, tumor-invasive lymphocyte areas 402-4, tumor-adjacent lymphocyte areas 402-5, stroma- and tumor-invasive lymphocyte areas 402-6, stroma-adjacent lymphocyte areas 402-7, tumor and stroma areas 402-8, and tumor-adjacent stroma areas 402-9. Each feature may be evaluated as to both a density or concentration (vertical axis) and a percentage (horizontal axis) of each feature in the images 102 of the tumors. The set of images of tumors may be further divided into a subset of training images, which may be used to train a machine learning classifier such as the neural networks 112-1, 112-2 to determine the features, and a subset of testing images, which may be used to evaluate the effectiveness of the machine learning classifiers in determining the features in previously unseen images of tumors. In this manner, the machine learning classifier may be validated to determine the consistency of the underlying logic when applied to new data. For example, the chart in FIG. 4 was developed based on diagnostic hematoxylin and eosin stain (H&E-stain) of pathology images of pancreatic adenocarcinoma patients who underwent chemotherapy.

It may be further desirable to characterize the tumors as one of several classes, such as low-risk tumors and high-risk tumors, on the basis of factors that are characteristic of tumors of each class. For example, tumors of respective classes may also be associated with different features, such as concentration and/or percentage of a particular type of tumor area (e.g., tumor-invasive lymphocytes), and differences in such characteristic features may enable the tumors of one class to be distinguished from tumors of another class. Further, different tumor classes may be associated with different clinical properties, such as responsiveness to various treatment options and prognosis such as survivability. In order to determine such clinical properties for a particular tumor in an individual, it may be desirable to determine the tumor class of the tumor in order to guide the selection of a diagnosis and/or treatment regimen for the individual.

FIG. 5 is an illustration of a classification of tumors of different classes based on a feature subset in accordance with some example embodiments.

In the comparison 500 of FIG. 5, the feature subset of selected features 506 with the images 504 of tumors is used to classify tumors as either a low-risk tumor class 502-1 and a high-risk tumor class 502-2 based on a percentages of areas in each image 504 of each class 502 corresponding to each of the features 506 of the feature subset. The high-risk class of tumors may be associated with a first survival probability, and the low-risk class of tumors may be associated with a second survival probability that is longer than the first survival probability. The percentages of the respective features 506 of the images 504 of the tumor classes 502 may be compared, for example, to determine the degree to which the features 506 are diagnostic of the respective tumor classes 502. For example, the images 504 of the high-risk tumor class 502-2 may demonstrate a smaller and more consistent range of values for the first feature 506-1 and the third feature 506-2 than for the images 504 of the low-risk tumor class 502-1. Also, the values for the third feature 506-3 may be typically higher in images of tumors of the low-risk tumor class 502-1 than in images of tumors of the high-risk tumor class 502-2. These measurements, which may be determined based on selected features 506 of the feature subsets of the tumor classes 502, may present clinically significant findings in the pathology of tumors of different tumor classes 502, and may be used by both clinicians and automated processes (such as diagnostic and/or prognostic machine learning processes) to classify tumors into different tumor classes 502. Further information regarding the labeling of images may be found, for example, in U.S. Pat. No. 10,346,712 ("Metric-Based Recognition, Systems and Methods"), the entirety of which is incorporated by reference as if fully reproduced herein. Further information regarding large-scale image recognition may be found, for example, in U.S. Pat. No. 10,796,196 ("Large Scale Image Recognition Using Global Signatures and Local Feature Information"), the entirety of which is incorporated by reference as if fully reproduced herein.

C. Region of Interest Determination

Machine learning models, such as the examples shown in FIGS. 2A, 2B, 3 and 4, may be applied to an image to identify tissue types, such as tumors, stroma, lymphocytes, as well as the relationships between such tissue types, such as tumor-infiltrating lymphocytes. As shown in FIG. 5, further techniques may be used to classify a tumor into one of several classes, such as a low-risk tumor class 502-1 and a high-risk tumor class 502-2.

However, a clinical diagnosis or selection of treatment options may involve a determination of an area of the tissue as a target for surgery or radiation chemotherapy, and it may be difficult to select such treatments to target a region of interest unless further information is provided, such as a boundary of the region of interest. Such further information about the image may depend upon additional consideration of the identified areas by a pathologist or clinician, which may be difficult or inefficient to apply to a large set of images. Instead, it may be desirable to provide a further automated analysis of the classified tissue types to determine a region of interest in the image. Further, it may be helpful to provide such a technique that is informed by the decision-making process of a pathologist or clinician. For example, in a semi-supervised machine learning model, "ground truth" images that have been labeled from a reference source are used to train a machine learning model, such as a convolutional neural network 110, to determine a region of interest based on a spatial distribution of the tissue types. Such a machine learning model may be capable of synthesizing the information of lower-level machine learning classifiers into determinations that are of clinical significance, in a similar manner to trained professionals, and may do so in an automated way that may provide greater efficiency.

D. Training Classifier to Determine Region of Interest

Figure 6A:
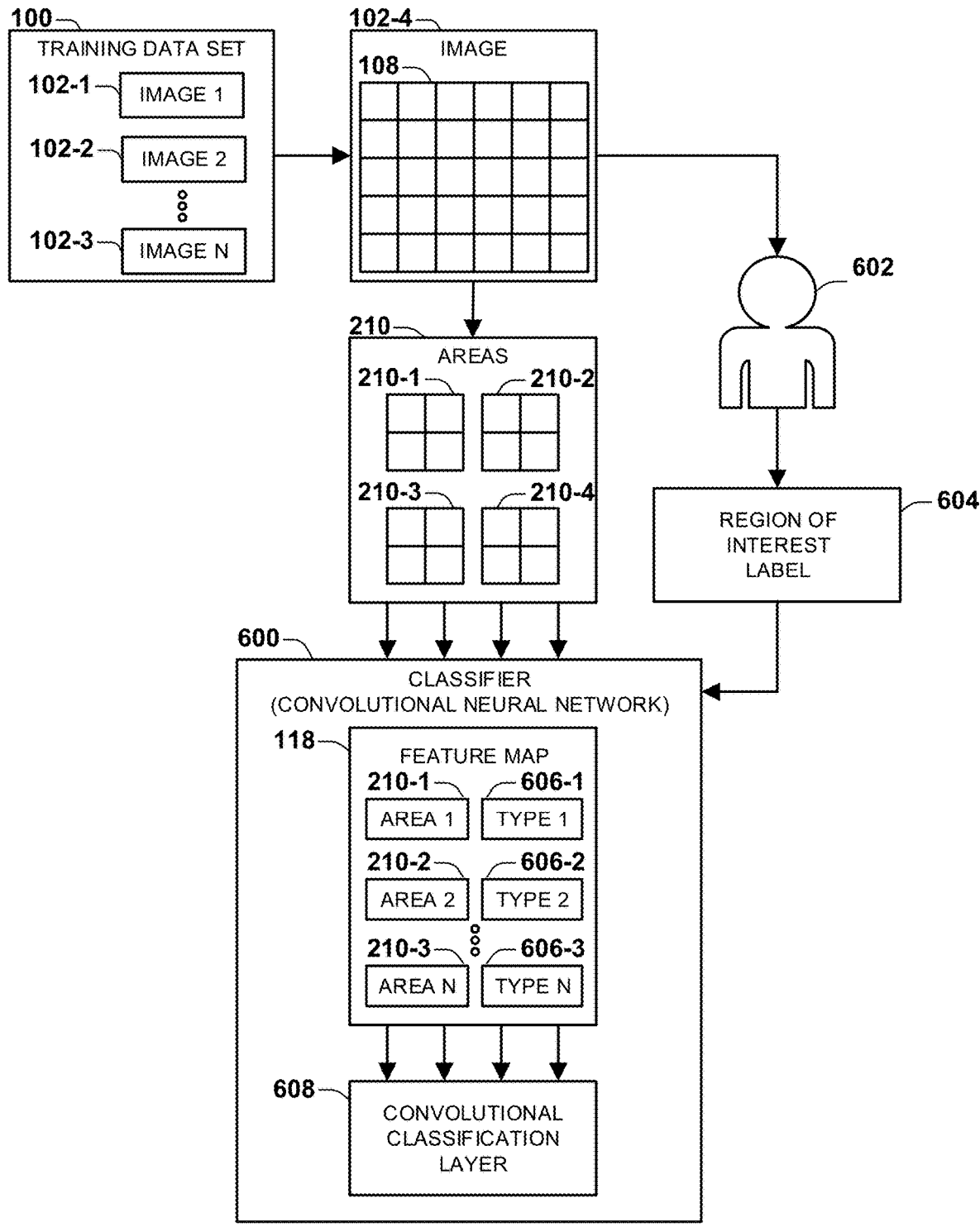
FIG. 6A is an illustration of an example scenario featuring a training of an example classifier to determine a region of interest of an image using a set of images of tissue samples in accordance with some example embodiments.

FIG. 6A is an illustration of an example scenario featuring a training of an example classifier to determine a region of interest of an image using a set of images of tissue samples in accordance with some example embodiments.

In FIG. 6A, a training data set 100 of images 102-1, 102-2, 102-3, etc. is provided to train a classifier 600. In the example scenario of FIG. 6A, the classifier 600 is a convolutional neural network 110, but it is to be appreciated that a variety of machine learning models or combinations thereof may be devised to operate as a classifier 600 in the techniques presented herein. The classifier 600 may include a classification layer 608 that is trained to output a desired region of interest label 604 for a region of interest in an image 102 in the following manner. An image 102-4 of the training data set 100 is selected, and a human labeler 602, such as a pathologist or a clinician, reviews the image 102-4 and provides a region of interest label 604. For example, the human labeler 602 may draw a boundary around an area that represents a region of clinical significance, such as a tumor. The human labeler 602 may base the determination of the region of interest label 604 on the visual features of the image 102, but also based on professional expertise, such as knowledge of anatomic structures, a medical history of the individual whose tissue is shown in the image 102, and visual artifacts in images 102 produced by an imaging modality such as x-ray or CT scans. Further, the pixels 108 of the image 102-4 are partitioned into an area set of areas 210-1, 210-2, 210-3, 210-4, such as 64×64-pixel blocks, or blocks of pixels that correspond to a physical scale, such as a 100 $\mu m^2$ area 210 of the image 102-4. For each area 210, a classifier 600 (such as a convolutional neural network 110, as one of several suitable types of machine learning models) may identify a tissue type 606-1, 606-2, 606-3 for each area 210-1, 210-2, 210-3 of the image 102-4. In some example embodiments, the identification of tissue types 606 for the respective areas 210 may be performed according to the techniques shown in FIGS. 2A and 2B. The classifier 600 may further compare the areas 210 with the region of interest label 604 determined by the human labeler 602 to determine whether the areas 210 of the image 102 are part of a region of interest, for example, such as whether the areas 210 are inside or outside the region of interest label 604 provided by the human labeler 602. Based on the comparison, a classification layer 608, such as a convolutional classification layer 120, may be trained to output a determination of the areas 210 of the image 102-4 that correspond to the region of interest label 604. Training the classifier 600, including a classification layer 608 such as a convolutional classification layer 120, on the set of images 102-1, 102-2, 102-3 of the training data set 100, according to region of interest labels 604 provided for each image 102, may produce a classifier 600 that is capable of determining regions of interest in the images 102 with a high degree of correspondence to the region of interest labels 604 provided by the human labeler 602.

Figure 6B:
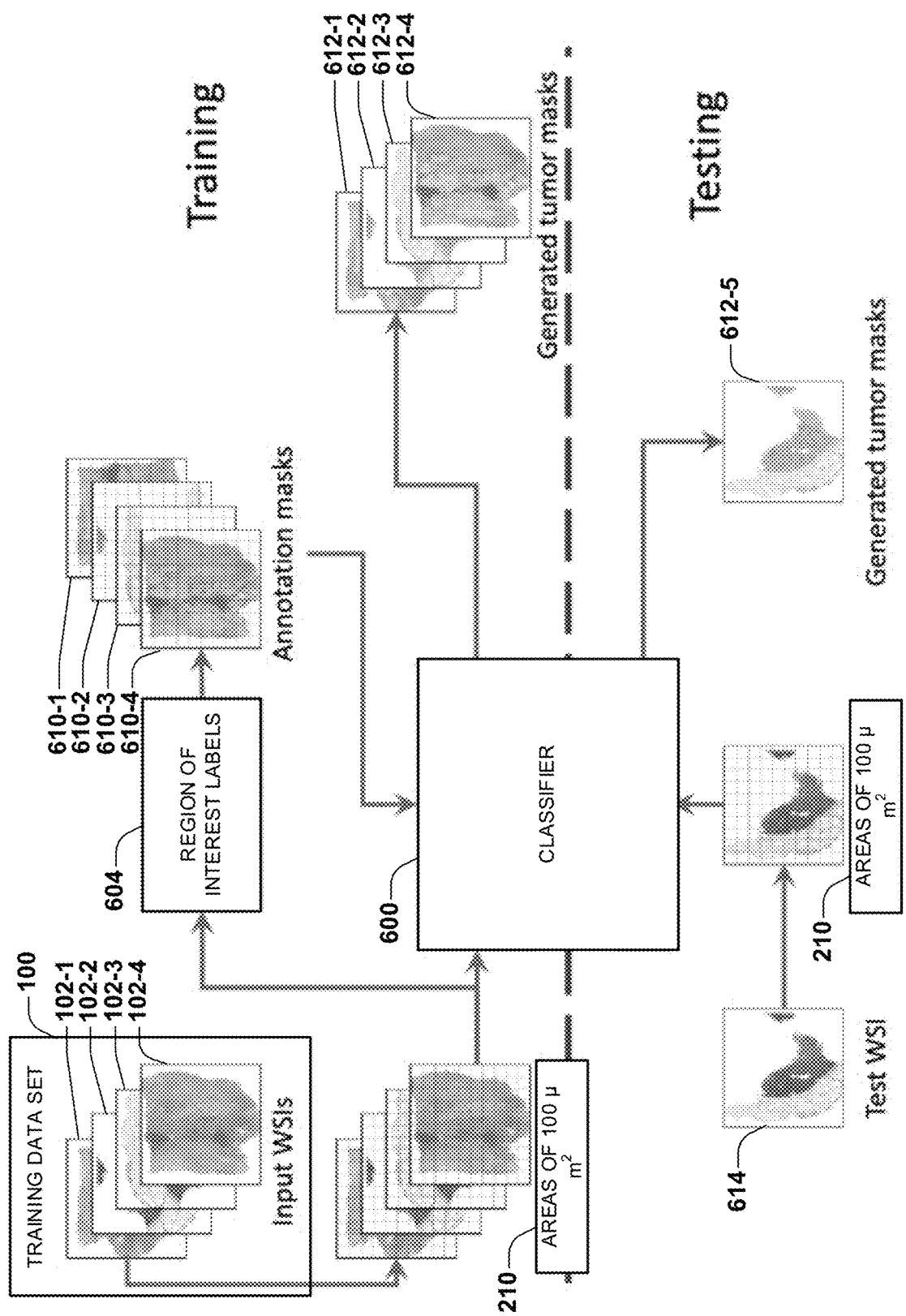
FIG. 6B is an illustration of an example scenario featuring a training and testing of an example classifier to determine a region of interest of an image using a set of images of tissue samples in accordance with some example embodiments.

FIG. 6B is an illustration of an example scenario featuring a training and testing of an example classifier to determine a region of interest of an image using a set of images of tissue samples in accordance with some example embodiments.

In FIG. 6B, a training data set 100 of images 102-1, 102-2, 102-3, etc. is again provided to train a classifier 600. In the example scenario of FIG. 6B, the classifier 600 is a convolutional neural network 110, but it is to be appreciated that a variety of machine learning models or combinations thereof may be devised to operate as a classifier 600 in the techniques presented herein. The classifier 600 may be configured to analyze areas 210 of an image 102 (such as 100 $\mu m^2$ areas of the image 102) and to produce a tumor mask 612 that indicates a region of interest. The area mask 612 may include, for example, an indication of a contiguous block of areas 210 of the image 100 that depict a region of interest.

In the example scenario of FIG. 6B, a set of region of interest labels 604 may be provided as a set of annotation masks 610-1, 610-2, 610-3, 610-4 is provided, wherein the annotations (that is, the region of interest labels 604) indicate one or more regions of interest in each of the images.

The annotation masks 610 may be used as "ground truth" determinations, and may be provided, for example, by a human labeler 602 or from a reference source, such as whole-slide images (WSIs) from The Cancer Genome Atlas Project (TCGA) (source: https://www.cancer.gov/about-nci/ organization/ccg/research/structural-genomics/tcga). The annotation masks 610 may be used to train the classifier 600, for example, to generate a set of tumor masks 612-1, 612-2, 612-3, 612-4 to analyze that respectively indicate a region of interest. The classifier 600 may be trained until the generated tumor masks 612 correspond to the annotation masks 610 with a reasonably high degree of confidence. The training of the classifier 600 may be further evaluated through a testing process in which a test image 614, such as an image 102 that is not part of the training data set 100, is evaluated by the classifier 600 to generate a tumor mask 612-5, and which may be compared with an annotation mask 610 to determine the accuracy with which the classifier 600 determines the region of interest in a previously unseen image 614. Successful testing of the classifier 600 may result in a fully trained classifier 600 that may be capable of determining regions of interest in new image 102 for which a generated tumor mask 612-5 may be used as an annotation mask 610, that is, as a determination of regions of interest in the image 102 that may at least correspond to how the image 102 would have been similarly evaluated by a human labeler 602.

Some variations in the development of a classifier 600 to determine a region of interest 702 of an image 102 in accordance with the techniques presented herein will now be described. It is to be appreciated that the following uses may be featured or used alternatively, concurrently, and/or together in various example embodiments.

In some example embodiments, the classifier 600 may be a convolutional neural network 110 including a classification convolutional layer 120 that has been trained to determine regions of interest 702 in images 102 based on the tissue types 606 of the set of areas 210 of the image 102, for example, using the tissue types 606 as a feature map provided by a last convolutional layer 112-3 preceding the convolutional classification layer 120. However, it is to be appreciated that a wide variety of machine learning models may be selected as the classifier 600 to determine the region of interest 702.

Some example embodiments may involve training a classifier 600 to generate at least one measurement of the region of interest 702 based on at least one visual feature of the set of areas 210 of the region of interest 702. For example, the at least one measurement may include one or more of: a size of the region of interest 702 (such as units of area or volume), a shape of the region of interest 702 (such as curvature), a symmetry of the region of interest 702 (such as a measurement of symmetry about a linear or radial axis), a color of the region of interest 702 (such as a color offset as measured in a color space), a density of the region of interest 702 (as indicated by color density and/or a count of features per unit area), or a moment of the region of interest 702. Alternatively or additionally, the at least one measurement may be determined by a non-learning technique, such as an image processing technique that calculates or measures a size of a region of interest 702 that has been determined by the classifier 600. Some example embodiments may store each of the at least one measurements, for example, as a quantitative measurement (e.g., the determined region of interest 702 is 5 mm in width) and/or as a qualitative measurement (e.g., the determined region of interest 702 is "large," due to having a size that is above a "large" threshold size).

Some example embodiments may involve storing a description of the region of interest 702 based on the tissue types 606 of the set of areas 210, and the classifier 600 may be configured to determine the region of interest 702 by matching the description of the region of interest 702 with the tissue types 606 of the set of areas 210. In some example embodiments, the description may include one or more of an area count, feature count (e.g., number of lymphocytes), density, perimeter length, maximum caliper measurement, circularity, and/or eccentricity of the region of interest 702. For example, the description may define a region of interest based on one or more of: a number of a subset of areas 210 of a tissue type 606, a size of a subset of areas 210 of a tissue type 606, a density of a subset of areas 210 of a tissue type 606, a moment of a subset of areas 210 of a tissue type 606, a shape of a subset of areas 210 of a tissue type 606, a symmetry of a subset of areas 210 of a tissue type 606, a spatial distribution of a subset of areas 210 of a tissue type 606, a visual appearance of a subset of areas 210 of a tissue type 606, or a distance between a subset of areas 210 of a first tissue type 606 and a subset of areas 210 of a second tissue type 606. In some example embodiments, a region of interest may be described as one or more moment orders of a distribution of features, such a first-order moment (e.g., mean); a second-order moment (e.g., variance); a third-order moment (e.g., skewness); and/or a fourth-order moment (e.g., kurtosis).

Some example embodiments may involve training the classifier 600 to determine a similarity measurement between the region of interest 702 in the image 102 and the region of interest 702 of the description. For example, the classifier 600 may be trained to compare visual features of the region of interest 702 and the visual features of the description and to determine whether such visual features are identical, similar, or dissimilar. The comparison may be performed, for example, based on the entire region of interest 702 (e.g., a shape, size, and/or symmetry of the boundary demarcating the region of interest 702) or based on the respective areas 210 within the region of interest 702 (e.g., counting the number of areas 210 within the region of interest 702 that have a density of lymphocytes above a determined threshold). Based on the comparison, a similarity measurement may be generated, for example, as a qualitative determination (e.g., a high, medium, or low degree of confidence that the region of interest 702 matches the description) or a quantitative determination (e.g., 95% of the areas 210 within the region of interest 702 match the description). In some example embodiments, the classifier 600 may be trained to determine the similarity measurement based on similarity measurements provided by a human labeler 602, such as a high, medium, or low degree of confidence of the human labeler 602 that the region of interest is a tumor. The training may involve training the classifier 600 to output similarity measurements that correspond to the similarity measurements provided by the human labeler 602. In some example embodiments, the classifier 600 may be trained to generate the description based on the training data set 100 of images 102, for example, based on a determination of visual features that commonly occur within the regions of interest 702 indicated in the training data set 100.

In some example embodiments, the classifier 600 may be configured to identify at least one area 210 of at least one image 102 of the training data set 100 that does not match the description, and to request information about the at least one area 210. For example, the classifier 600 may determine that an area 210 or a subset of areas 210 of at least one image 102 are difficult to identify as any particular tissue type 606, or whether an area 210 or a subset of areas 210 are a region of interest 702. For example, classifier 600 may determine that an area 210 or a subset of areas 210 are a borderline or low-confidence match with the description of the region of interest 702, and/or have a low similarity measurement, such that a determination of the area 210 or subset of areas 210 as a region of interest 702 is inconclusive. In such cases, the classifier 600 may request information about the at least one area 210, for example, requesting a human labeler 602 to identify a tissue type 606 for the at least one area 210, and/or requesting a human labeler 602 to indicate whether the at least one area 210 is or is not a region of interest 702. In some example embodiments, the classifier 600 may retrain based on receiving the information, such that output of the classifier 600 for images 102 including similar areas 210 correspond to the received information. In some example embodiments, the classifier 600 may update the description of the region of interest 702 based on receiving the information, for example, to include or exclude the areas 210 from determinations of areas of interest 702. In some example embodiments, the classifier 600 may exclude the inconclusively determined image 102 from the training data set 100 until and unless receiving the information to clarify the inconclusive determination. In this manner, the classifier 600 may be iteratively trained to account for more difficult or low-confidence images 102, based on the guidance and input of a human labeler 602, to improve the determinations of the regions of interest 702. Further, this semi-supervised training process may conserve the time and attention of the human labeler 602, for example, by asking the human labeler 602 to provide additional region of interest labels 604 only for images 102 for which the classifier 600 is unable to provide a conclusive determination of the region of interest 702.

In some example embodiments, the description may be generated based on information provided by a user, such as a human labeler 602 who may interact with the example embodiment. For example, a user interface may receive, from the user, an indication of a region of interest 702 in one or more of the images 102 of the training data set 100, such as a circle drawn around the region of interest 702 with a pointing device, or a selection of a cluster of areas 210 that are included in the region of interest 702. The example embodiment may generate the description based on features of the one or more images 102 of the training data set 100 and the indication received from the user. Some example embodiments may generate such a description by partitioning the image 102 of the training data set 100 into a set of areas 210, determining the areas 210 of the image 102 of the training data set 100 that are within the region of interest 702 indicated by the user, and determining at least one visual feature of the areas 210 of the image 102 of the training data set 100 that are within the region of interest 702 indicated by the user. Alternatively or additionally, a user may provide a description of regions of interest 702 in other ways, such as indicting a set of tissue types 606 that are associated with the region of interest, or a relationship between a first tissue type 606 and a second tissue type 606 that indicates the region of interest 702, such as areas 210 classified as lymphocytes that are within a proximity or threshold distance of areas 70 classified as tumor. The parameters may be specified and/or adjusted by the user (e.g., a selection or adjustment of the threshold distance of areas 210 classified as lymphocytes that are within 200 µm of areas 210 classified as tumor), or may be learned from the indication of the region of interest 702 identified by the user (e.g., determining that regions of interest 702 often have areas 210 classified as lymphocytes that are within 200 µm of areas 210 classified as tumor).

Some example embodiments may store a first description of a tissue type of a first region type, and a second description of a tissue type of a second region type that is different than the first region type. As a first such example, the first description may describe a cancerous tissue region type, and the second description may describe a noncancerous tissue region type. As a second such example, the first description may describe a first cancer region type, and the second description may describe a second cancer region type that is different than the first cancer region type. The classifier 600 may be trained to determine a first region of interest 702 in the images 102 of the training data set 100 by matching the set of areas 210 of each image 102 with the first description of the first region type, and to determine a second region of interest 702 in the images 102 of the training data set 100 by matching the set of areas 210 of each image 102 with the second description of the second region type. That is, the classifier 600 may be trained to identify different types of regions of interest 702, such as different tumor types that present with different appearances, such as different sizes, shapes, symmetries (such as circularity and/or eccentricity), colors, or the like. Further, the classifier 600 may be configured to determine whether one or both types of regions of interest 702 are present in an image 102.

As a first such example, a shape may be evaluated based on a comparison of a shape of a feature with a typical, expected, and/or predefined two-dimensional shape, such as a circle, oval, or polyhedron, or the like, and by evaluating a divergence of shape of the feature from the typical, expected, and/or predefined shape (e.g., as a ratio of the areas and/or a gap between the compared boundaries). As a second such example, a symmetry of a feature may be evaluated based on an evaluation of a divergence of the feature with respect to a linear or rotational axis. For example, the circularity of a visual feature may be identified by determining a centroid of the feature as a radial axis, and by determining the variance of a distance of a boundary of the visual feature to the centroid for respective angles about the radial axis within the plane of the image. Similarly, the linearity of a visual feature may be identified by determining a linear axis, such as a length, of a visual feature and determining the variance of an orthogonal distance between the linear axis and a corresponding linear boundary of the visual feature at various points along the linear axis. Alternatively or additionally, the classifier may be configured to determine whether a region of interest 702 more closely matches the first description or the second description, that is, to distinguish between region of interest types. For example, the classifier 600 may be trained to determine that a similarity measurement between the region of interest 702 in the image 102 and regions of interest 702 of the first description is greater than a similarity measurement between the (same) region of interest 702 in the image 102 and regions of interest 702 of the second description (or vice versa).

In some such embodiments, a human labeler 602 may provide an indication of whether a region of interest 702 in one or more images 102 of the training data set 100 is more similar to the first region type or the second region type, and the classifier 600 may be trained to distinguish between the region types in the regions of interest 702 in the images 102 of the training data set 100 in a manner that corresponds to the indication provided by the human labeler 602. In some example embodiments, a description of a region of interest may be encoded as a description of an entire image (e.g., an image may be indicated as showing a tumor of a selected type based on a determination of that a region of interest 702 within the image matches the description of the region of interest 702, even if other areas of the image do not match the description of the region of interest 702). In some example embodiments, the description may be represented as one or more statistic (e.g., the image is determined to show a tumor as a region of interest in which 20% of the cells shown in the regions of interest are above a threshold size and/or have a threshold shape irregularity).

In some example embodiments, the classifier 600 may be trained to determine a spatial relationship between areas 210 of a first tissue type 606 and areas 210 of a second tissue type 606. Such spatial relationships may be evaluated, for example, as a distance between boundaries of areas 210 of the same, similar, or different tissue types; as a distance between a centroid of a first area 210 and a centroid of a second area 210; as a mean distance between a first group of areas 210 for a first tissue type 606 and a second group of areas 210 for a second tissue type 606; or the like. Examples of such spatial relationships include: a union between the areas 210 of the first tissue type 606 and the areas 210 of the second tissue type 606, an intersection between the areas 210 of the first tissue type 606 and the areas 210 of the second tissue type 606, a complement between the areas 210 of the first tissue type 606 and the areas 210 of the second tissue type 606, or a distance between the areas 210 of the first tissue type 606 and the areas 210 of the second tissue type 606. As an example, the classifier 600 may be trained to determine that some areas 210 are tumor tissue types 606 and that some areas 210 are lymphocyte tissue types 606, and, further, that a distance between the areas 210 that include lymphocytes are within a threshold distance of the areas 210 that are tumor tissue types 606. Based on such a determination, these areas 210 that lymphocyte tissue types 606 may be determined to be tumor-invasive lymphocytes (TILs). Some example embodiments may further include generating a measurement of the spatial relationship between the areas 210 of the first tissue type 606 and the areas 210 of the second tissue type 606, such as a size, shape, symmetry, or density of the union or intersection, or a mean distance between the areas 210 that include lymphocytes are within a threshold distance of the areas 210 that are tumor tissue types 606. Alternatively or additionally, the spatial relationship may be determined by a non-learning technique, such as an image processing technique that identifies, calculates, and/or measures the spatial relationship. Some example embodiments may store the spatial relationship and/or the measurement thereof, for example, as a quantitative measurement (e.g., 50 lymphocyte areas 210 of an image 102 are determined to be tumor-invasive lymphocyte areas) and/or as a qualitative measurement (e.g., "most" of the lymphocytes are tumor-invasive lymphocytes).

In some example embodiments, the classifier 600 may be trained to determine one or more outcomes of an individual whose tissue is shown in an image 102 based on the determination of the region of interest 702 in the image 102. For example, a human labeler 602 may provide one or more outcome labels, such as a diagnosis of the individual based on the region of interest 702, a prognosis of the individual based on the region of interest 702, or a treatment of the individual based on the region of interest 702. The classifier 600 may be trained to generate outcomes of the individuals based on the images 102 that match the outcome labels provided by the human labeler 602.

Many such classifiers 600 may be trained to produce output that corresponds to "ground truth" output (such as provided by a human labeler 602 or by a reference source, such as TCGA) in accordance with the techniques presented herein.

E. Determining and Presenting Region of Interest

Figure 7:
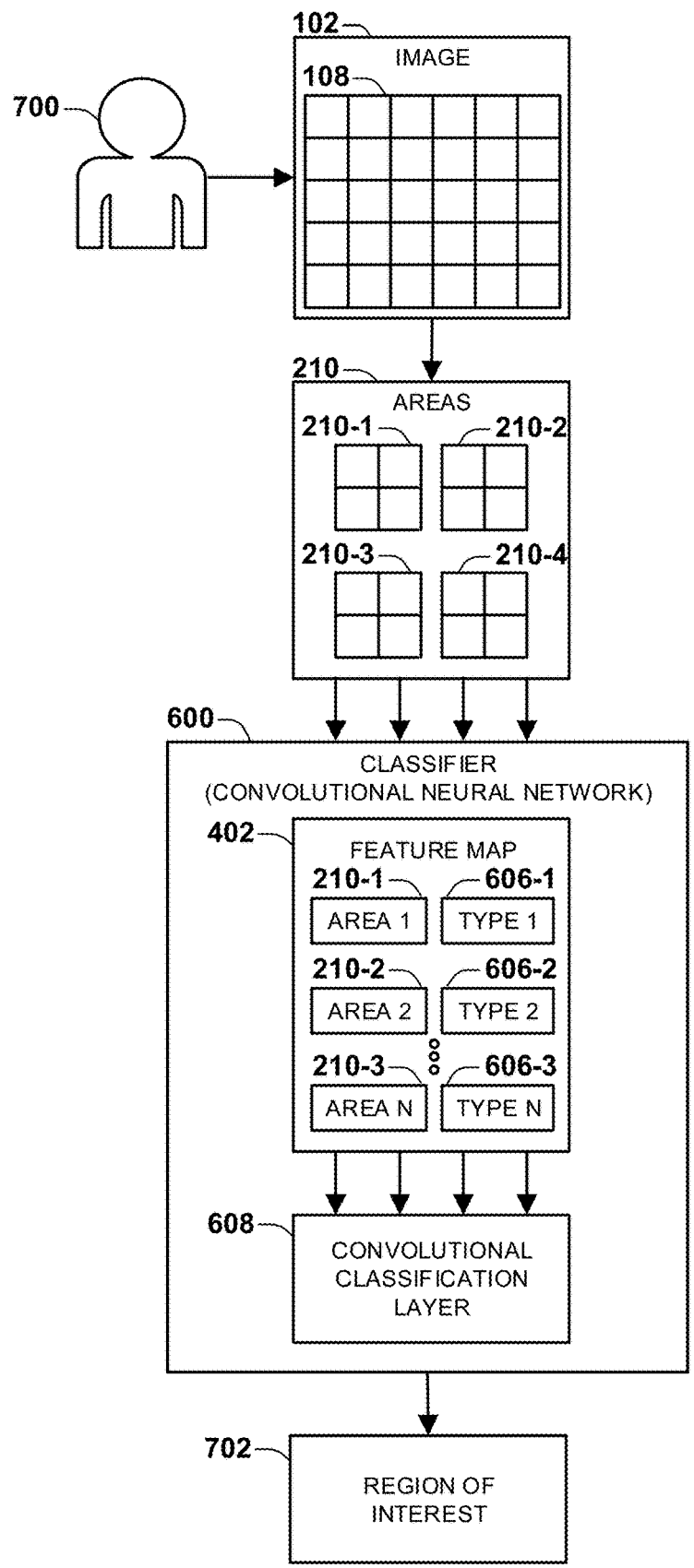
FIG. 7 is an illustration of an example scenario featuring a determination of a region of interest in an image of a tissue sample using an example classifier in accordance with some example embodiments.

FIG. 7 is an illustration of an example scenario featuring a determination of a region of interest 702 in an image 102 of a tissue sample using an example classifier 600 in accordance with some example embodiments.

In the example scenario of FIG. 7, an image 102 is provided that depicts tissue of an individual 700, such as a patient with a health condition from whom tissue has been removed and stained according to pathology protocols. The pixels of the image 102 may be partitioned into a set of areas 210, such as 100 $\mu m^2$ areas. A classifier 600 may identify a tissue type 606 for each area 210. In some example embodiments, the identification of tissue types 606 for the respective areas 210 may be performed according to the techniques shown in FIGS. 2A and 2B.

The classifier 600 may further evaluate the areas 210 and tissue types 606 as a feature map 118, which may be evaluated by a classification layer 608 that has been trained to determine a region of interest 702 in the image 102, such as a tumor mask 612 as shown in FIG. 6B. In the example scenario of FIG. 7, the classifier 600 is a convolutional neural network, but it is to be appreciated that a variety of machine learning models or combinations thereof may be devised to operate as a classifier 600 in the techniques presented herein. The region of interest 702 may be determined by the classifier 600, for example, as a boundary that demarcates the region of interest within the image 102, and/or as a marking of the pixels 108 of the image 102 that are within the region of interest 702. The region of interest 702 determined by the classifier 600 may be used for a variety of clinical applications, such as a determination of an area of the tissue as a target for surgery or radiation chemotherapy. In this manner, the classifier 600 may automatically determine a region of interest 702 of the image 102 that may closely match a determination of the region of interest label 604 that would have been selected by a human labeler 602, such as a pathologist or a clinician, in accordance with the techniques presented herein.

Some variations in the uses of the region of interest 702 of an image 102 determined in accordance with the techniques presented herein will now be described. It is to be appreciated that the following uses may be featured or used alternatively, concurrently, and/or together in various example embodiments.

Some example embodiments may present an image 102 to a user with various types of indications of a region of interest 702. For example, the image 102 may be presented with the region of interest 702 shown with a distinctive visual appearance, such as a color, shading, highlighting, pattern, or the like; a visual boundary demarcating areas 210 that are within the region of interest 702 from areas 210 that are outside the region of interest 702; and/or one or more annotations, such as arrows or text labels of the region of interest 702. Some example embodiments may evaluate images represented to a variety of one-channel or multi-channel color spaces (e.g., RGB, HSV, grayscale, etc.), and may evaluate such images on the basis of the features of each individual channel (e.g., evaluating the features of R, G, and B channels separately); on the basis of a combination of channels (e.g., converting an RGB image to a one-channel intensity image, such as grayscale); and/or on the basis of the combination of channels (e.g., applying a convolutional filter that detects features based on corresponding sets of R, G, and B color channels for respective pixels of an image). Some example embodiments may generate at least one mask indicating the areas 210 of one tissue type 606 among the set of areas 210, and present the image 102 including the at least one mask. Some example embodiments may present the image 102 with an indicator of the set of areas 210 of the image 102 that are determined as the region of interest 702, such as by storing a mask indicating a labeled region of interest 702 and presenting, with the image, an indicator of the labeled region of interest.

As previously discussed, some example embodiments may include a classifier 600 that has been trained to determine regions of interest 702 according to a stored description of the region of interest 702, which based on the tissue types 606 of the set of areas 210. Such example embodiments may be further configured to, in addition to determining and presenting a region of interest 702 in an image 102, present the description of the region of interest 702 upon which the determination is based. For example, the example embodiment may indicate one or more details of the description that match the region of interest 702 as an explanation of why the presented region of the image 102 has been determined to be a region of interest 702. Such details may include, for example, a number of a subset of areas 210 of a tissue type 606, a size of a subset of areas 210 of a tissue type 606, a density of a subset of areas 210 of a tissue type 606, a moment of a subset of areas 210 of a tissue type 606, a shape of a subset of areas 210 of a tissue type 606, a symmetry of a subset of areas 210 of a tissue type 606, a spatial distribution of a subset of areas 210 of a tissue type 606, a visual appearance of a subset of areas 210 of a tissue type 606, or a distance between a subset of areas 210 of a first tissue type 606 and a subset of areas 210 of a second tissue type 606.

As previously discussed, some example embodiments may include a classifier 600 that has been trained to determine a similarity measurement between the region of interest 702 in the image 102 and the region of interest 702 of the description. Such example embodiments may be further configured to, in addition to determining and presenting a region of interest 702 in an image 102, present the similarity measurement, such as an indication of a degree of confidence that the identified region of the image 102 is a region of interest 702. In some example embodiments, a similarity between regions of interest may be identified as a measurement of a similarity of a feature between two regions of interest 702 (e.g., a measurement or ratio of a similarity in size, shape, color, symmetry, or the like); a measurement of a difference of a feature between two regions of interest 702 (e.g., a measurement or ratio of a difference in size, shape, color, or offset); and/or an aggregate measurement of similarity or difference of a set of features (e.g., a sum or product of the similarity measurements or difference measurements of size, shape, and/or symmetry between two regions of interest 702). The similarity measurement may be presented as a qualitative measurement (e.g., an indication of a high, medium, or low confidence of the determination) and/or as a quantitative measurement (e.g., an indication that 95% of the areas 210 within the region of interest 702 match the description).

As previously discussed, some example embodiments may include a classifier 600 that has been trained to determine at least one area 210 of the image 102 that does not match the description. Such example embodiments may be further configured to, in addition to determining and presenting a region of interest 702 in an image 102, present an indication of the at least one area 210 that does not match the description. For example, the example embodiment may present a specific indication that some areas 210 of the image are not regions of interest 702, such as non-tumor areas or non-tissue areas. In some example embodiments, such areas 210 of the image 102 may be shown in a contrasting visual appearance with respect to the region of interest 702, such as a color, shading, highlighting, pattern, or the like that contrasts with the corresponding visual appearance of the region of interest 702. In some example embodiments, such areas 210 of the image 102 may be excluded or masked out, such that only the region of interest 702 is presented. Alternatively or additionally, if the determination of some areas 210 of the image 102 as matching any of one or more stored descriptions are inconclusive, an example embodiment may present an indication that the areas 210 are inconclusive (e.g., may or may not be a tumor), and/or a request for information about the at least one area 210. In some example embodiments, upon receiving the information (e.g., an indication from a user, such as a human labeler 602, that the at least one area 210 is a particular tissue type 606 and/or region type), the presentation of the image 102 may be updated based on the received information, and/or the classifier 600 may be retrained based on the received information.

As previously discussed, some example embodiments may store a first description of a tissue type of a first region type and a second description of a tissue type of a second region type that is different than the first region type, such as descriptions of a cancerous tissue region type and a noncancerous tissue region type, and/or descriptions of a first cancer region type, and a second cancer region type that is different than the first cancer region type. In addition to determining one or more regions of interest 702 in an image 102 based on the first description and the second description, the example embodiment may present the regions of interest 702 with different visual appearances to indicate the respective region types (e.g., presenting a region of interest 702 based on the first description with a first visual appearance, such as a color, shading, highlighting, pattern, or the like, and presenting a region of interest 702 based on the second description with a second visual appearance that is different than the first visual appearance, such as a different color, different highlighting, a different shading, a different pattern, or the like). Alternatively or additionally, for a region of interest 702 that matches both the first description and the second description, the example embodiment may distinguish the region of interest 702 as more closely matching the first description than the second description, or vice versa, and may indicate such determination as part of the presentation. For example, upon determining that a similarity measurement between the region of interest 702 in the image 102 and regions of interest 702 of the first description is greater than a similarity measurement between the region of interest 702 in the image 102 and regions of interest 702 of the second description, the example embodiment may choose the first visual appearance for the region of interest 702 instead of the second visual appearance, or vice versa. Some example embodiments may present the image 102 with a first mask of a first tissue type with a first indicator, or a second mask of a second tissue type with a second visual indicator that is different than the first visual indicator.

As previously discussed, some example embodiments may involve presenting, with the image 102, at least one measurement of the region of interest 702 based on at least one visual feature of the set of areas 210 of the region of interest 702. For example, the at least one measurement may include one or more of: a size of the region of interest 702, a shape of the region of interest 702, a symmetry of the region of interest 702, a color of the region of interest 702, a density of the region of interest 702, or a moment of the region of interest 702. The at least one measurement may have been determined by a classifier 600 and/or a non-learning technique, such as an image processing technique that calculates or measures a size of a region of interest 702 that has been determined by the classifier 600. In addition, such example embodiments may present the at least one measurements with the image, for example, as a quantitative measurement (e.g., an indication that the determined region of interest 702 is 5 mm in width) and/or as a qualitative measurement (e.g., an indication that the determined region of interest 702 is "large," due to having a size that is above a "large" threshold size).

In some example embodiments, the at least one measurement may include one or more of: a size of the region of interest 702, a shape of the region of interest 702, a symmetry of the region of interest 702, a color of the region of interest 702, a density of the region of interest 702, or a moment of the region of interest 702. Such example embodiments may be further configured to output the at least one measurement with the presentation of the image 102, such as a quantitative measurement (e.g., a size of a tumor), a qualitative measurement (e.g., an indication that a tumor is "large," "medium," or "small"), a text label, or the like.

As previously discussed, some example embodiments may include a classifier 600 that has been trained to determine a spatial relationship between areas 210 of a first tissue type 606 and areas 210 of a second tissue type 606, such as a union between the areas 210 of the first tissue type 606 and the areas 210 of the second tissue type 606, an intersection between the areas 210 of the first tissue type 606 and the areas 210 of the second tissue type 606, a complement between the areas 210 of the first tissue type 606 and the areas 210 of the second tissue type 606, or a distance between the areas 210 of the first tissue type 606 and the areas 210 of the second tissue type 606. Some example embodiments may further include presenting the image including the spatial relationship presented with a visual appearance, such as a color, highlighting, shading, pattern, or the like. For example, the areas 210 classified as lymphocyte tissue types 606 may be shown in a first color, and a subset of the areas 210 that have been further determined to be tumor-invasive lymphocytes may be shown in a second color that is different than the first color, and/or by highlighting or drawing a boundary around the subset of tumor-invasive lymphocyte areas 210 that distinguishes from the non-tumor-invasive lymphocyte areas 210.

As previously discussed, some example embodiments may generate a measurement of the spatial relationship between the areas 210 of the first tissue type 606 and the areas 210 of the second tissue type 606, such as a size, shape, symmetry, or density of the union or intersection, or a mean distance between the areas 210 that include lymphocytes are within a threshold distance of the areas 210 that are tumor tissue types 606. Alternatively or additionally, the presentation of the image may include a presentation of the measurement of the spatial relationship, such as a quantitative measurement (e.g., a text label indicating that 50 lymphocyte areas 210 of an image 102 are determined to be tumor-invasive lymphocyte areas) and/or as a qualitative measurement (e.g., a text label indicating that "most" of the lymphocytes are tumor-invasive lymphocytes).

As previously discussed, some example embodiments may include a the classifier 600 that has been trained to determine one or more outcomes of an individual whose tissue is shown in an image 102 based on the determination of the region of interest 702 in the image 102, such as a diagnosis of the individual 700 based on the region of interest 702, a prognosis of the individual 700 based on the region of interest 702, or a treatment of the individual 700 based on the region of interest 702. The user may be, for example, the individual 700 with a health condition such as a tumor; a family member or guardian of the individual 700; or a healthcare provider for the individual 700, including a physician, nurse, or clinical pathologist. The clinical value and/or the output may be, for example, one or more of: a diagnosis for the individual 700, a prognosis for the individual 700, a survivability of the individual 700, a classification of the region of interest 702 such as a tumor, a diagnostic and/or treatment recommendation for the region of interest 702, or the like. Such example embodiments may further include, in the presentation of the image, an indication of an outcome of the individual 700 based on the image 102. For example, the determination of a region of interest 702 based on the techniques disclosed herein may be used to determine and output, for the user, a clinical value for an individual 700.

Some example embodiments may use the determination of the region of interest 702 to display a visualization of the clinical value (such as the prognosis) for the individual 700. For example, a terminal may accept an image 102 of a tumor of an individual 700, and, optionally, a set of clinical features, such as the individual's demographic features, clinical observations of the individual 700 and the region of interest 702, and measurements of the region of interest 702. The terminal may apply the techniques presented herein (e.g., processing the image by a classifier 600, such as a convolutional neural network) to determine the region of interest 702, and optionally to determine other properties of the region of interest 702, such as a classification of a tumor as one of a low-risk tumor class and a high-risk tumor class, and/or a prognosis that is associated with individuals 700 with tumors of the tumor class. The clinical value may be determined, for example, as a survivability, such as projected survival durations and probabilities, optionally including a confidence or accuracy of each probability. In some example embodiments, the clinical value may be presented as a visualization, such as a Kaplan Meier survivability projection of the individual 700 based on analysis of the region of interest 702. In some example embodiments, the visualization may include additional information about the region of interest 702, such as one or more of the masks 302 that indicate the area types of the areas of the image 102; measurements 304 of the image 102, such as a concentration for each area type (e.g., a concentration of lymphocytes in one re more areas as determined by binning), and/or a percentage area of the area type as compared with the entire image 102. In some example embodiments, the visualization may include additional information about the individual 700, such as the individual's clinical features, and may indicate how respective clinical features contribute to the determination of the clinical value (such as the prognosis) for the individual 700.

Some example embodiments may use the determination of the region of interest 702 to determine, and to display for a user, a diagnostic test for a health condition indicated by the region of interest 702 based on the clinical value (such as the prognosis) for the individual 700. For example, based on a tumor being determined as a region of interest 702 and being classified as a low-risk class by the tumor analysis model, an apparatus may recommend less aggressive testing to further characterize the tumor, such as blood tests or imaging. Based on the tumor being classified as a high-risk class by the tumor analysis model, an apparatus may recommend more aggressive testing to further characterize the tumor, such as a biopsy. Some example embodiments may also display, for the user, an explanation of the basis of the determination; a set of options for further testing; and/or a recommendation of one or more options to be considered by the individual 700 and/or a healthcare provider.

Some example embodiments may use the determination of the region of interest 702 to determine, and to display for a user, a treatment of the individual 700 based on the clinical value (such as the prognosis) for the individual 700. For example, based on the region of interest 702 being classified as a tumor in a low-risk class, an apparatus may recommend less aggressive treatment of the tumor, such as less aggressive chemotherapy. Based on the region of interest 702 being classified as a tumor in a high-risk class, an apparatus may recommend more aggressive treatment of the tumor, such as more aggressive chemotherapy and/or surgical removal. Some example embodiments may also display, for the user, an explanation of the basis of the determination; a set of options for further testing; and/or a recommendation of one or more options to be considered by the individual 700 and/or a healthcare provider.

Some example embodiments may use the determination of the region of interest 702 to determine, and to display for a user, a schedule of a therapeutic agent for treating the tumor based on the clinical value (such as the prognosis) for the individual 700. For example, based on the region of interest 702 being classified as a tumor in a low-risk class, an apparatus may recommend chemotherapy with a lower frequency, at a later date, and/or with a lower dosage. Based on the region of interest 702 being classified as a tumor in a high-risk class, an apparatus may recommend more aggressive treatment of the tumor, such chemotherapy with a higher frequency, at an earlier date, and/or with a higher dosage. Some example embodiments may also display, for the user, an explanation of the basis of the determination; a set of options for further testing; and/or a recommendation of one or more options to be considered by the individual 700 and/or a healthcare provider. Many such types of classification and output of clinical values for the individual and information about the health condition indicated by the region of interest 702 may be provided in some example embodiments.

F. Experimental Results

Figure 11:
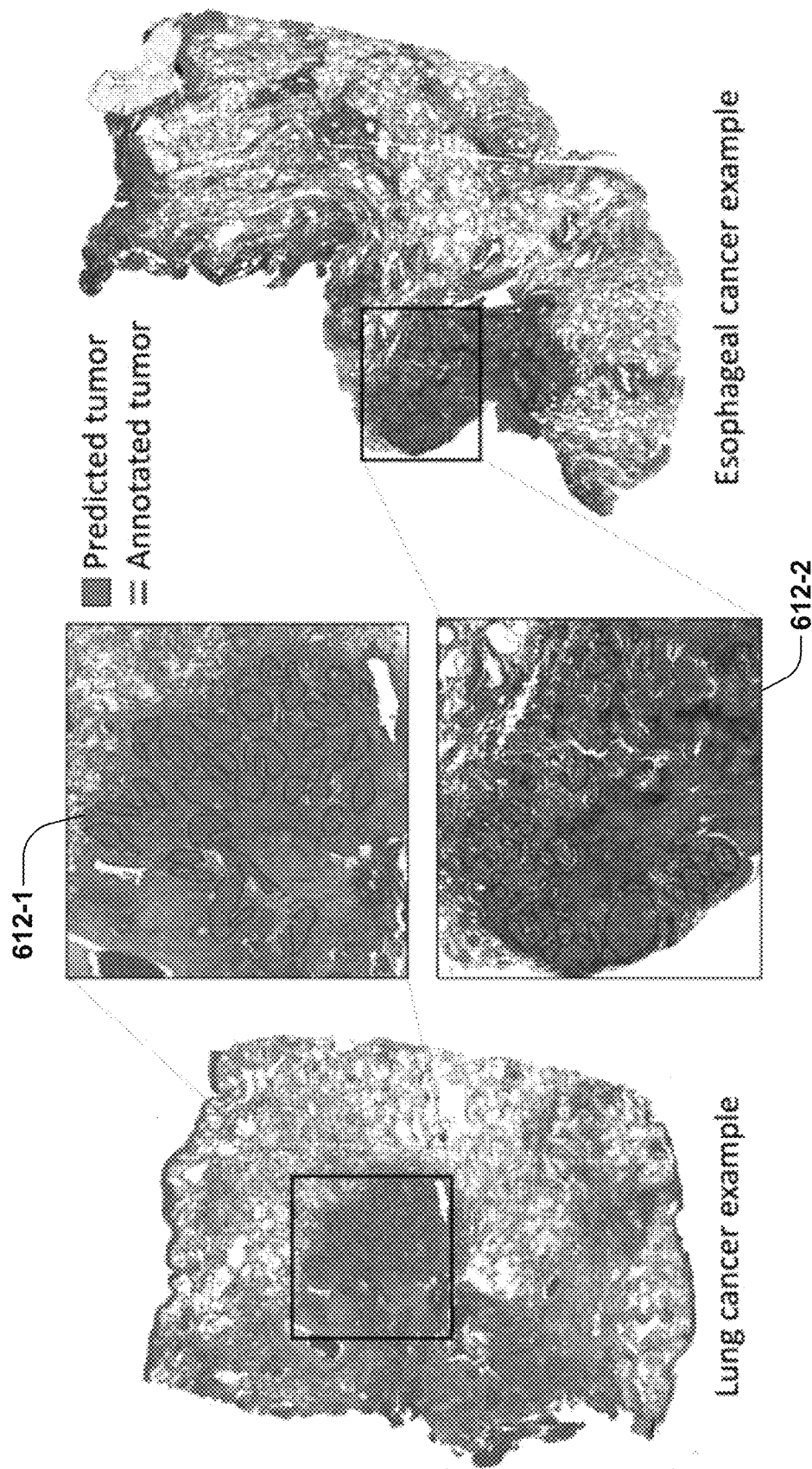
FIG. 11 is an illustration of an example set of masks indicating regions of interest in tissue samples, in accordance with the techniques presented herein.

FIG. 11 is an illustration of an example set of tumor masks indicating regions of interest in tissue samples, in accordance with the techniques presented herein. FIG. 11 shows tumor masks 612-1, 612-2 (indicated in brown) generated by an example embodiment of the techniques presented herein that indicate regions of interest in the form of possible tumor areas, and a comparison with the boundaries of an annotated tumor (indicated by blue lines), as determined by a human labeler. FIG. 11 demonstrates a high degree of correspondence of the determinations of regions of interest 702 and "ground truth" images prepared by human labelers.

FIGS. 12A-12C are a set of comparative illustrations of a set of labeled images and experimental results of using a classifier 600 to determine a region of interest 702 in accordance with the techniques presented herein. These experimental results were obtained by applying a trained Inception v3 convolutional neural network to generate tumor masks 612 that indicate a region of interest 702 in a whole-slide image 102 (WSI) from The Cancer Genome Atlas Project (TCGA), for comparison with an annotation mask 610 provided by a human labeler 602, in accordance with the techniques presented herein.

In FIGS. 12A, 12B, and 12C, one visual example from each of 18 TCGA cancer types that were evaluated by an example embodiment. an image 102 of a particular type of tumor from a TCGA WSI is shown at left at 5× magnification. At center, an image 102 of the tumor including an annotation mask 610 provided by a human labeler 602 is shown, wherein the region of interest 702 is shown as a green mask overlaying a purple background. At right, a comparative image 102 of a generated tumor mask 612 indicating the region of interest 702 is shown as a yellow mask overlaying a purple background, as well as a total count of the patches or areas 210 that are within the region of interest 702. A comparison of the intersection of the annotation mask 610 and the generated tumor mask 612 is indicated as an accuracy of the machine learning model in determining the region of interest 702 in a similar manner as the human labeler 602. For example, TCGA-GM-A2DF-01Z-00-DX1, which is an image of a breast cancer tumor, was partitioned into 18,653 areas, of which 94% of were correctly classified as tumor vs. non-tumor when compared with a human-labeled ground truth.

Figure 13A:
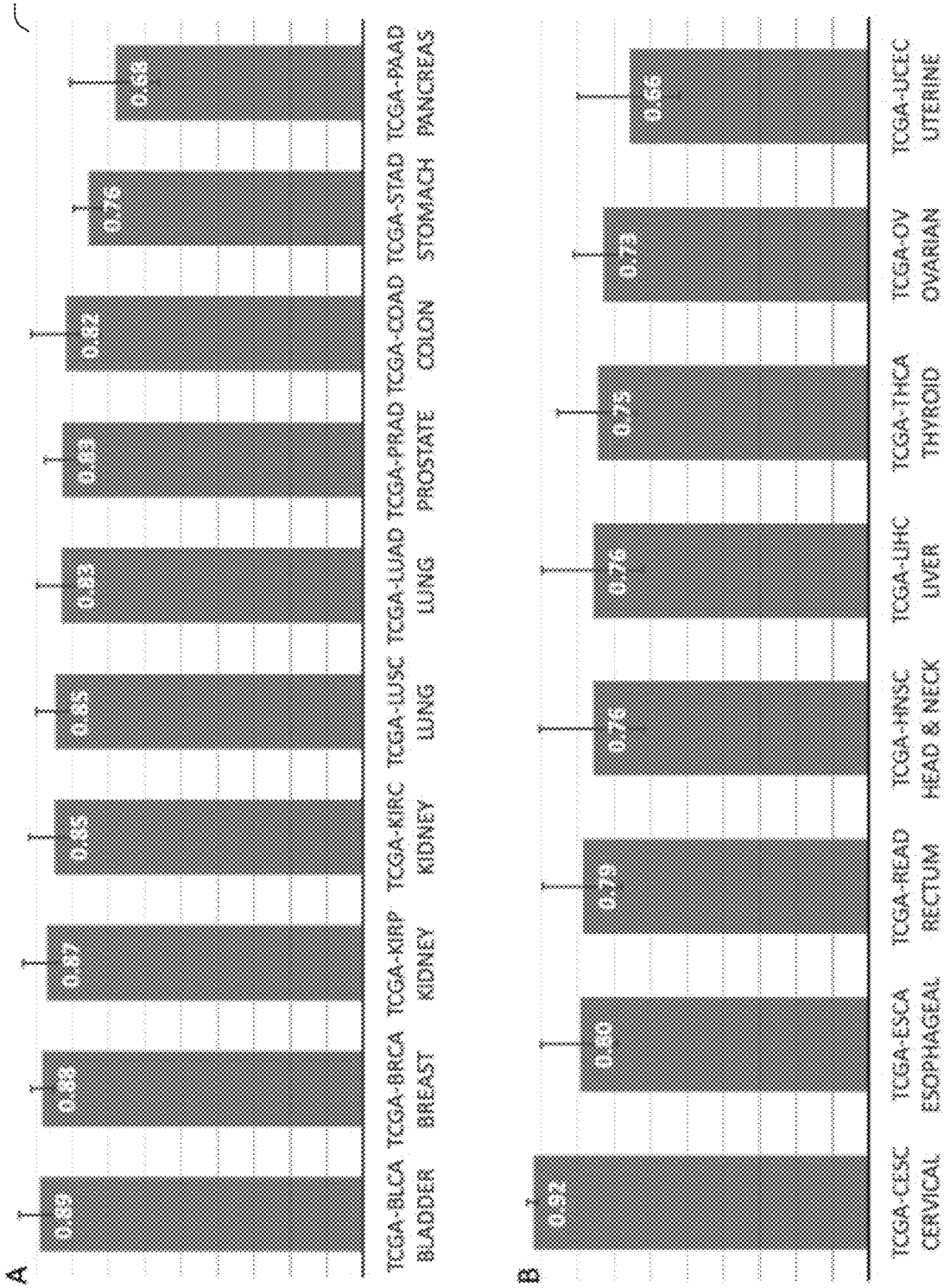
FIG. 13A is an illustration of a first set of experimental results of using a classifier to determine different region types of regions of interest in accordance with the techniques presented herein.
Figure 13B:
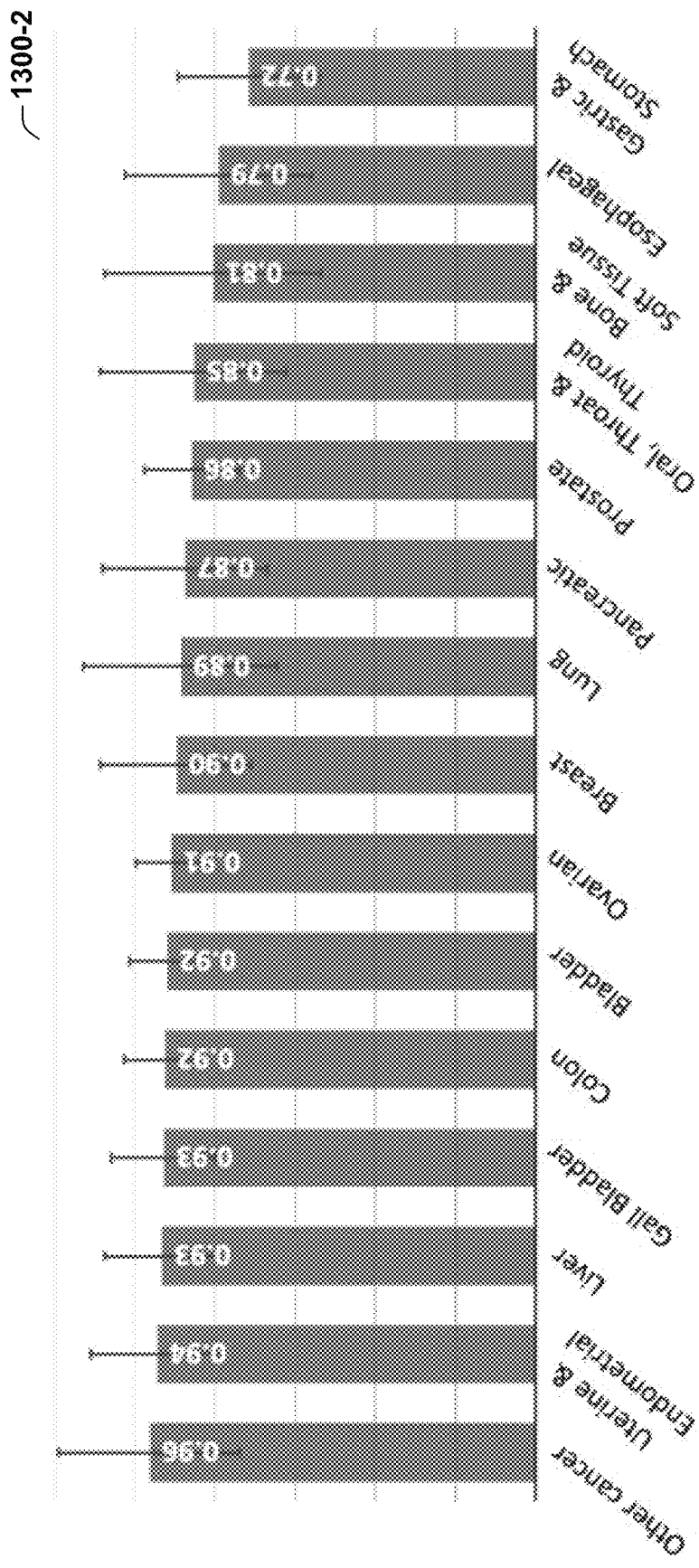
FIG. 13B is an illustration of a second set of experimental results of using a classifier to determine different region types of regions of interest in accordance with the techniques presented herein.

Each of FIGS. 13A and 13B is an illustration of a set of experimental results of using a classifier 600 to determine different region types of regions of interest 702 in accordance with the techniques presented herein, and, in particular, regions that indicate different types of cancer based on a set of 118 TCGA WSIs. Each of the results in each of FIGS. 13A and 13B is presented as an aggregate or average accuracy, similar to the accuracy indicators shown in FIGS. 12A, 12B, and 12C. The results indicate that the generated tumor masks 612 for various types of tumors, generated by a classifier 600 trained in accordance with the techniques presented herein, generally match the corresponding annotation masks 610 provided by a human labeler 602 for a range of tumor types. For example, FIG. 13A shows several whole-slide images (WSIs) for each of the 18 TCGA cancer types. Each image was partitioned into an average of 22,023 areas of 100-micron square areas. TCGA-COAD colon cancer WSIs were determined to present the least number of areas identified within regions of interest per WSI (15,327 areas per WSI on average), while TCGA-BRCA breast cancer were determined to have the greatest number of areas identified within regions of interest (27,448 areas per WSI on average). FIG. 13A shows a high correspondence between the evaluation of TCGA-CESC (cervical), TCGA-BLCA (bladder) and TCGA-BRCA (breast) cancers by an example embodiment as compared with the ground-truth images from TCGA. FIG. 13B shows clinical samples that were obtained, evaluated by pathologists for at a resolution suitable for laser-capture microdissection (LCM, and tumor-rich area (i.e., >80% tumor) were identified and marked. For each sample, if sufficient tumor tissue were marked, then the pathologist could stop labeling images, as the labeling of regions outside of the annotations as being tumor or non-tumor areas. To overcome this limitation, true positive tumor areas were used as a performance criterion. That is, a classifier 600 of an example embodiment was trained on TCGA-only data in order to identify all regions that were marked by the pathologist as tumor. FIG. 13B shows per-cancer tumor identification results based on the evaluation of 186 clinical WSIs.

G. Technical Effects

Some example embodiments that include a determination of a region of interest 702 using a classifier 600 trained in accordance with the techniques presented herein analysis may exhibit a variety of technical effects or advantages, especially in the computer-based embodiments disclosed herein.

A first example of a technical effect that may be exhibited by some example embodiments is a more consistent determination of regions of interest 702 in images 102 of tissue types of an individual 700 than may be achieved by a human labeler 602. For example, determinations of regions of interest labels 604 by a human labeler 602 may be subjective, biased, and/or variable, wherein even a human labeler 602 examining the same image 102 on different days or under different conditions may generate different region of interest labels 604. By contrast, a classifier 600 trained to recognize regions of interest 702 would typically produce a same determination of a region of interest 702 irrespective of a time and/or circumstances in which the image 102 is so evaluated, without subjective bias.

A second example of a technical effect that may be exhibited by some example embodiments is a more accurate determination of regions of interest 702 in images 102 of tissue types of an individual 700 than may be achieved by a human labeler 602. For example, the determinations of regions of interest labels 604 by a human labeler 602 may be based on the qualitative analyses by the human labeler 602 of visual features such as size, shape, symmetry, color, density, and proximity. By contrast, a classifier 600 trained to recognize regions of interest 702 may take into account precise quantitative measurements, such as a quantitative measurement of the number, density, and proximity of lymphocytes to tumor tissue. Such classifiers 600 may use a rich and deep set of quantitative measurements, such as different numbers or a different density of lymphocytes at respective distances or proximities to a tumor, than may be factored in by a well-trained human labeler 602. As a result, such computer-based classifiers 600 may be capable of more nuanced and accurate determinations of regions of interest 702 well beyond the capabilities of a human.

A third example of a technical effect that may be exhibited by some example embodiments is a generalized determination of regions of interest 702 in images 102 of tissue types of an individual 700. For example, a classifier 600 trained to determine a region of interest 702 based on one type of tumor may also be capable of determining a region of interest 702 based on another type of tumor with a similar appearance or characteristics, such as a tumor of a similar appearance arising in a different type of tissue, subject, or circumstance. Such classifiers 600 may use transfer learning to determine regions of interest 702 involving new and/or rare types of tumors that have not yet been seen by pathologists or clinicians.

A fourth example of a technical effect that may be exhibited by some example embodiments is a more efficient allocation of resources based upon such analyses. For example, reliance upon a human labeler 602 to determine regions of interest 702 in a large number of images 102 may be costly and/or may involve an extended period of time. Further, the accuracy of the human labeler 602 may vary proportionally with a number of images 102 so evaluated; that is, the human labeler 602 may have to choose between evaluating the images 102 quickly or accurately. In other cases, a human labeler 602 may be unavailable, such as due to illness, vacation, or short-staffing considerations, and the return of pathology results may be delayed, which may delay diagnosis and/or treatment of the individuals 700 whose tissue is depicted in the images 102. By contrast, classifiers 600 that are trained based on the techniques presented herein may be capable of processing images 102 to determine regions of interest 702 both quickly and accurately, which may enable high-quality pathology results to be returned more quickly, and with a reduced cost as compared with the time and attention of a human labeler 602. In some cases, the classifier 600 may be included in automated processing facilities, such as robotic slide preparation, to improve the automated provision of medical diagnostic capabilities.

In some cases, the classifier 600 may be capable of processing slides faster or more efficiently; with a higher resolution, area, and/or count of slides per sample. In some cases, the classifier 600 may be capable of extracting more data and producing a more detailed analysis of a smaller amount or volume of material; for example, the techniques presented herein, as compared with other techniques such as human labeling, may produce a similar amount and/or quality of data about a sample based on a smaller volume of extracted tissue or a smaller number of slides. In some example embodiments, a classifier 600 may be used in conjunction with a human labeler, such as a pathologist, where the output of the classifier 600 may be used to distinguish between images that are labeled with low confidence (e.g., an image that closely matches a description of a tumor) and images that are not labeled with high confidence (e.g., an image that is inconclusively classified as tumor or non-tumor). The human labeler may be notified of the images with low-confidence classifications, and may be asked to evaluate and/or label only these images, while the images with high-confidence determinations may not be further considered by the human labeler. Alternatively or additionally, some high-confidence classifications may be of higher priority than other high-confidence classifications (e.g., a determination of an aggressive tumor type vs. a determination of a non-aggressive tumor type or a negative determination), and the human labeler may be requested to evaluate the image to verify, clarify, or correct the determination. As an example, images in which lymphocytes regions are within or near tumor areas (which may indicates an aggressive tumor) could be weighted (e.g., given more attention by the human labeler) in comparison to lymphocytes buried in stroma areas. Having signs of hot tumor gets the attention of the pathologist. In these cooperative examples, the attention of the human labeler may be selectively applied to the images for which further evaluation is desired (e.g., images of low confidence and/or high priority), and may be conserved by not requesting the human labeler to evaluate the high-confidence and/or low-priority images. Further, the evaluation of the low-confidence images by the human labeler could be used for further training of the classifier 600, for example, by retraining the classifier 600 to provide improved classifications of the low-confidence images. Many such technical effects may be achieved through the generation and use of classifiers 600 in accordance with the techniques presented herein.

H. Example Embodiments

Figure 8:
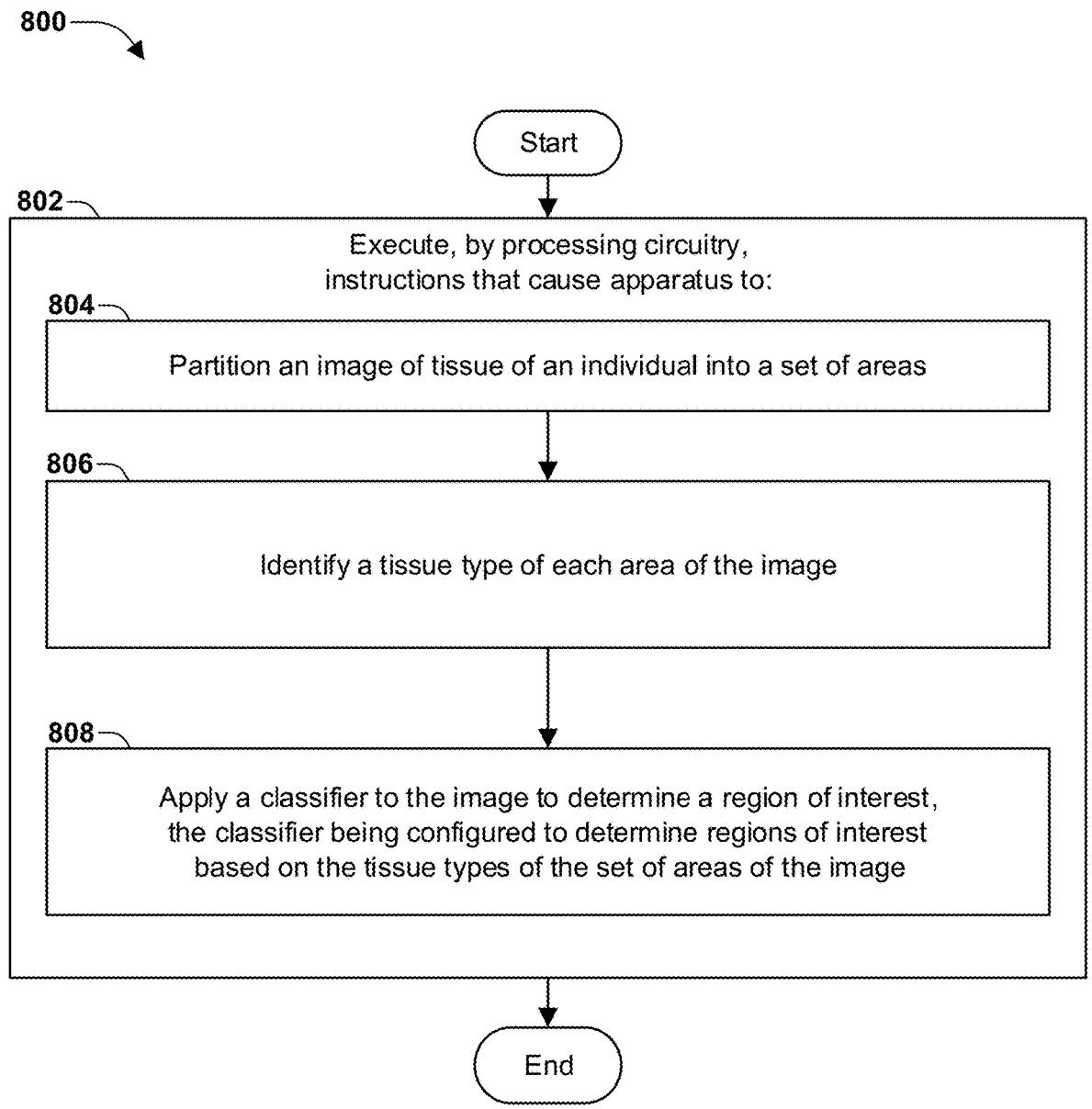
FIG. 8 is a flow diagram of an example method, in accordance with some example embodiments.

FIG. 8 is a flow diagram of an example method 800, in accordance with some example embodiments.

The example method 800 may be implemented, for example, as a set of instructions that, when executed by processing circuitry of an apparatus, cause the apparatus to perform each of the elements of the example method 800. The example method 800 may also be implemented, for example, as a set of instructions that, when executed by processing circuitry of an apparatus, cause the apparatus to provide a system for components, including an image evaluator, a first classifier configured to identify tissue types of areas of images, and a second classifier configured to determine regions of interest based on the tissue types of sets of areas of images, that interoperate to provide a system for classifying tumors.

The example method 800 includes executing 802, by processing circuitry of an apparatus, instructions that cause the apparatus to perform a set of elements. For example, the execution of the instructions may cause the apparatus to partition 804 an image 102 of tissue of an individual 700 into a set of areas 210. For example, the execution of the instructions may cause the apparatus to identify 806 a tissue type 606 of each area 210 of the image 102. For example, the execution of the instructions may cause the apparatus to apply 808 a classifier 600 to the image 102 to determine a region of interest 702, the classifier 600 being configured to determine regions of interest 702 based on the tissue types 606 of the set of areas 210 of the image 102. In this manner, the execution of the instructions by the processing circuitry may cause the apparatus to perform the elements of the example method 800, and so the example method 800 ends.

Figure 9:
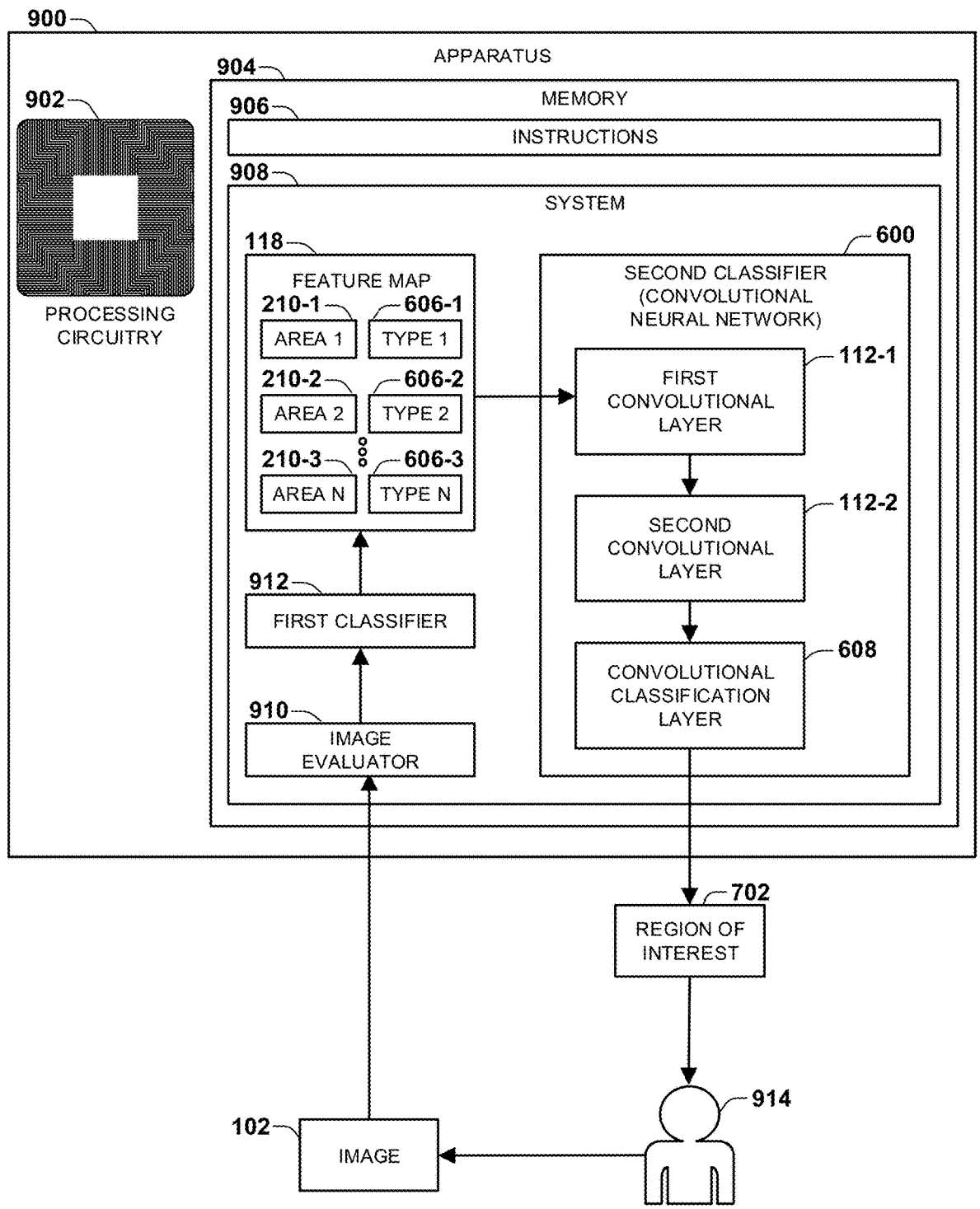
FIG. 9 is a component block diagram of an example apparatus, in accordance with some example embodiments.

FIG. 9 is a component block diagram of an example apparatus, in accordance with some example embodiments.

As shown in FIG. 9, some example apparatuses 900 may include processing circuitry 902 and a memory 904. The memory 904 may store instructions 906 that, when executed by the processing circuitry 902, cause the example apparatus 900 to determine a region of interest 702 in an image 102 of tissue of an individual 700. In some example embodiments, execution of the instructions 906 may cause the example apparatus 900 to instantiate and/or use a set of components of a system 908. While FIG. 9 illustrates one such system 908, some example embodiments may system 908 may embody any of the methods disclosed herein.

The example system 908 of FIG. 9 includes an image evaluator 910 that is configured to partition the image 102 into a set of areas 210. The image evaluator 910 may be, for example, an image processing algorithm that divides the image 102 into areas 210 of a certain size, such as areas 210 that correspond to 100 μm² patches of the image 102, or areas 210 of a certain pixel shape or count, such as 64×64 square pixel areas. The image evaluator 910 may partition the image 102 uniformly for all portions and areas 210 of the image 102, and/or may choose different partitions for different portions of the image 102, such as a higher-resolution area 210 for a first portion of the image 102 that may be a region of interest 702 and a lower-resolution area 210 for a second portion of the image 102 that is unlikely to be a region of interest 702.

The example system 908 of FIG. 9 includes a first classifier 912 configured to identify a tissue type 606 of each area 210 of the image 102. The first classifier 912 may be, for example, a convolutional neural network configured to classify each area 210 as being of a selected tissue type 606 based on the visual features of the area 210. In some example embodiments, the first classifier 912 may involve non-convolutional learning models and/or non-learning techniques, such as simple thresholding based on colors or shapes, and/or a combination of such models and techniques, such as an ensemble.

The example system 908 of FIG. 9 includes a second classifier 600 configured to determine a region of interest 702 of the image 102, the second classifier 600 being configured to determine regions of interest 702 based on the tissue types 606 of the set of areas 210 of the image 102. In the example apparatus 900 of FIG. 9, the second classifier 600 is a convolutional neural network including a first convolutional layer 112-1 that receives the output of the first classifier 912 as a feature map 118 of the areas 210 and tissue types 606 and provides output as input a second convolutional layer 112-2, which provides output as input to a convolutional classification layer 608 that determines whether any subset of the areas 210 is a region of interest 702. In some example embodiments, the second classifier 600 may involve non-convolutional learning models and/or non-learning techniques, such as simple thresholding based on colors or shapes, and/or a combination of such models and techniques, such as an ensemble.

The determination of the region of interest 702 may then be presented to a user 914, who may be the individual 700, a family member or guardian of the individual 700, a healthcare provider for the individual 700, including a physician, nurse, or clinical pathologist. In this manner, the example apparatus 900 and example system 908 provided thereon may determine the region of interest 702 in the image 102 in accordance with some example embodiments.

As shown in FIG. 9, some example apparatuses 900 may include processing circuitry 902 that is capable of executing instructions. The processing circuitry 902 may include, such as hardware including logic circuits; a hardware/software combination, such as a processor executing software; or a combination thereof. For example, a processor may include, but is not limited to, a central processing unit (CPU), a graphics processing unit (GPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

As further shown in FIG. 9, some example apparatuses 900 may include a memory 904 storing instructions 906. The memory 904 may include, for example, random-access memory (RAM), read-only memory (ROM), an erasable programmable read-only memory (EPROM), an electrically erasable programmable read-only memory (EEPROM), etc. The memory 904 may be volatile, such as system memory, and/or nonvolatile, such as a hard disk drive, a solid-state storage device, flash memory, or magnetic tape. The instructions 906 stored in the memory 904 may be specified according to a native instruction set architecture of a processor, such as a variant of the IA-32 instruction set architecture or a variant of the ARM instruction set architecture, as assembly and/or machine-language (e.g., binary) instructions; instructions of a high-level imperative and/or declarative language that is compilable and/or interpretable to be executed on a processor; and/or instructions that are compilable and/or interpretable to be executed by a virtual processor of a virtual machine, such as a web browser. A set of non-limiting examples of such high-level languages may include, for example: C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Swift, Eiffel, Smalltalk, Erlang, Ruby, Flash®, Visual Basic®, Lua, MAT- LAB, SIMULINK, and Python®. Such instructions 906 may also include instructions for a library, resource, platform, application programming interface (API), or the like that is utilized in determining a clinical value (such as a prognosis) for an individual based on a tumor shown in an image.

As shown in FIG. 9, some example systems 908 may be organized in a particular manner, for example, to allocate some functionality to each component of a system. Some example embodiments may implement each such component in various ways, such as software, hardware (e.g., processing circuitry), or a combination thereof. In some example embodiments, the organization of the system may vary as compared with some other example embodiments, including the example system 908 shown in FIG. 9. For example, some example embodiments may include a system featuring a different organization of components, such as renaming, rearranging, adding, partitioning, duplicating, merging, and/or removing components, sets of components, and relationships thereamong, without departing from the scope of the present disclosure. All such variations that are reasonably technically and logically possible, and that are not contradictory with other statements, are intended to be included in this disclosure, the scope of which is to be understood as being limited only by the claims.

Figure 10:
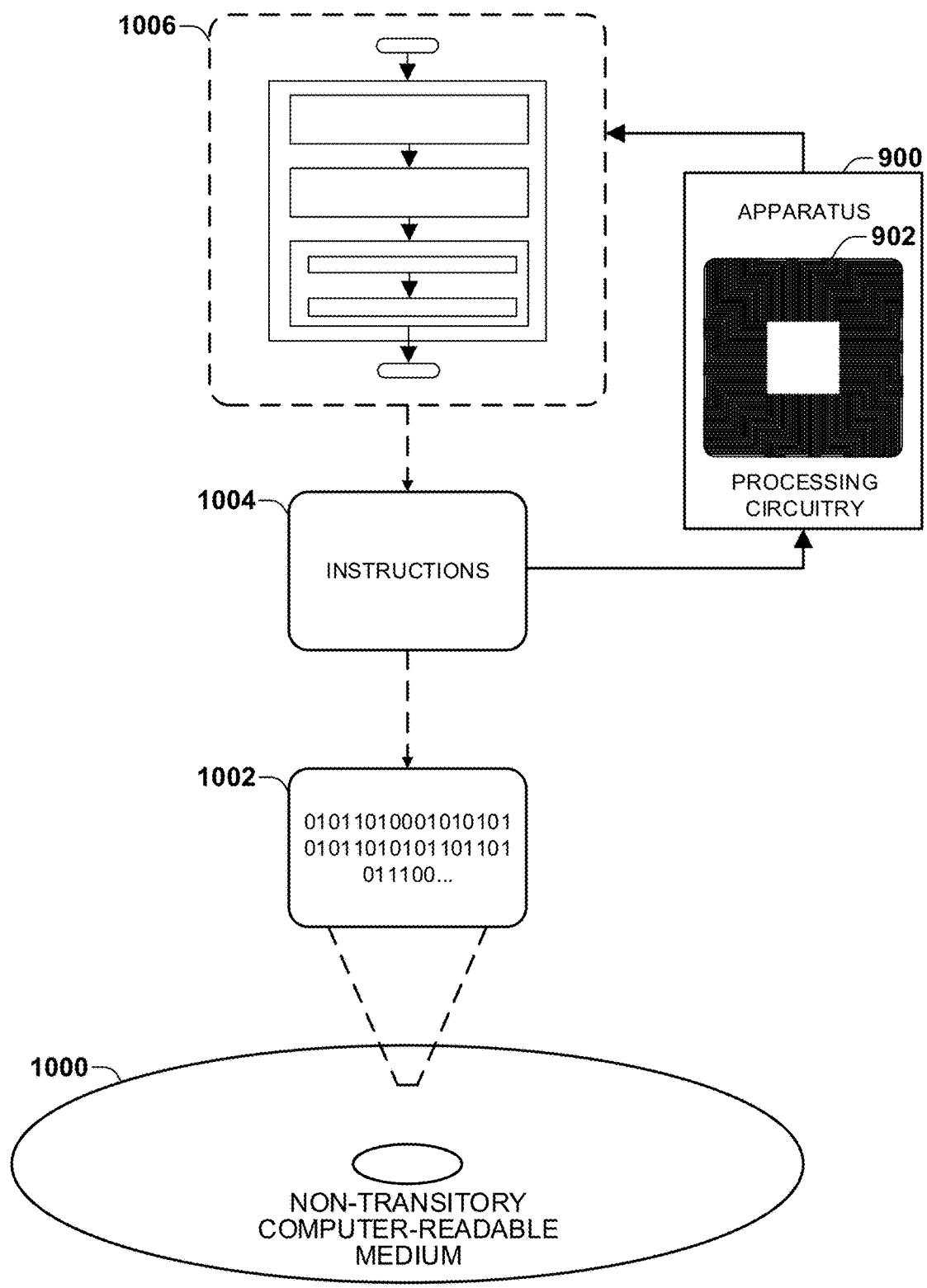
FIG. 10 is an illustration of an example computer-readable medium, in accordance with some example embodiments.

FIG. 10 is an illustration of an example computer-readable medium 1000, in accordance with some example embodiments.

As shown in FIG. 10, the non-transitory computer-readable medium 1000 may store binary data 1002 encoding a set of instructions 1004 that, when executed by processing circuitry 902 of an example apparatus 900, cause the example apparatus 900 to determine a clinical value (such as a prognosis) for an individual based on a tumor shown in an image in accordance with some example embodiments. As a first such example, the instructions 1004 may encode the elements of an example method 1006, such as the example method 800 of FIG. 8. As a second such example, the instructions 1004 may encode the components of the example apparatus 900 of FIG. 9. As a third such example, the instructions 1004 may encode the components of the example system 908 of FIG. 9.

In some example embodiments, a system may include image evaluating means for partitioning an image 102 of tissue of an individual 700 into a set of areas 210, a first classifying means for identifying a tissue type 606 of each area 210 of the image 102, and a second classifying means for determining a region of interest 702 in the image 102, the second classifying means further determining regions of interest 702 based on the tissue types 606 of the set of areas 210 of the image 102.

I. Variations

Some example embodiments of the present disclosure may include variations in many aspects, and some variations may present additional advantages and/or reduce disadvantages with respect to other variations of these sand other techniques. Moreover, some variations may be implemented in combination, and some combinations may feature additional advantages and/or reduced disadvantages through synergistic cooperation. The variations may be incorporated in some example embodiments (e.g., the example method of FIG. 8, the example apparatus 900 and example system 908 of FIG. 9, and/or the example non-transitory computer-readable medium 1000 of FIG. 10) to confer individual and/or synergistic advantages upon such example embodiments.

I1. Scenarios

Some example embodiments may be utilized in a variety of scenarios that involve an analysis determination of regions of interest 702 using machine learning models. For example, some example embodiments may use the disclosed techniques to determine regions of interest 702 for endeavors in various fields of life sciences, including healthcare and biomedical research.

In some example embodiments, the classifier 600 may be a convolutional neural network 110 featuring one or more convolutional layers, such as shown in FIG. 1, wherein a first convolutional layer 112-1 receives an image 102 and generates a first feature map 118-1 based on a first set of convolutional filters, and a second convolutional layer 112-2 receives the first feature map 118-2 and generates a second feature map 118-2 based on a second set of convolutional filters, etc. Such a classifier 600 may include a classification layer 608, such as a convolutional classification layer 120 that receives a last feature map 118-3 and performs a classification 122 of a region of interest 702 based on the last feature map 118-3. One such convolutional neural network 110 is an Inception v3 convolutional model, but other models convolutional neural networks 110 may be trained as a classifier 600 in accordance with the techniques presented herein. Further, non-convolutional machine learning models may be trained as a classifier 600 in accordance with the techniques presented herein, including support vector machines, restricted Boltzmann machines, sequential models, and attention-based models, as well as combinations thereof.

In some example embodiments, the training data set 100 may include images 102 of a variety of health conditions. While the examples presented herein involve tissue types such as tumors, it is to be appreciated that a classifier 600 may be trained in accordance with the techniques presented herein to determine other regions of interest in images 102 of tissue of an individual, such as lesions, plaques, clots, areas of infection or inflammation, anatomic anomalies, implants, foreign bodies, and the like, as well as normal or abnormal anatomic features such as blood vessels, bone, muscle, tendons, and the like. The region of interest 702 may be a variety of cancer types, including (without limitation) lung cancer tumors, pancreatic adenocarcinoma tumors, and/or breast cancer tumors.

In some example embodiments, the classifier 600 may be trained to identify any of a variety of recognizable features, such as shapes, sizes, colors, edges, gradients, and/or patterns. In some example embodiments, the classifier 600 may operate in cooperation with an image processing technique that initially recognizes and/or verifies the recognition of such features (e.g., receiving detected features from an image processing technique as a low-level feature map that is further classified by the classifier 600). As an example, the OpenCV image processing package provides a number of image processing techniques that are capable of detecting features, such as SIFT (Scale-Invariant Feature Transform), SURF (Speeded-Up Robust Features), DAISY (An Efficient Dense Descriptor Applied to Wide Baseline Stereo), and various Canny edge detection techniques. Further information regarding feature detection, such as edge descriptors, may be found, for example, in U.S. Pat. No. 10,229,342 ("Image-Based Feature Detection Using Edge Vectors"), the entirety of which is incorporated by reference as if fully reproduced herein.

In some example embodiments, the classifier 600 may be trained to identify regions of interest 702 based on a comparison of images taken at different times, such as a time series of images of a tissue sample or physiological feature of an individual. In some such cases, the classifier 600 may determine a region of interest based on a change of the region of interest 702 over time, such as a change in size, shape, density, location, color, symmetry, relationship to other areas, or the like. In some cases, the change may be measured as an absence of change (e.g., a resistance of a region of interest 702 to a treatment that changes other regions of interest 702). In some cases, the change may be measured based on the region of interest 702 over time; in other cases, the change of a region of interest 702 may be measured relative to a corresponding change of other regions of interest 702 (e.g., a first region of interest 702 that is growing faster over time than other regions of interest 702). In some cases, such change may be measured as a difference, a rate (e.g., a growth rate), and/or a rate difference (e.g., an increase in a growth rate). Analyses of change of the region of interest 702 over time may be useful, for example, in a determination or confidence of a classification, diagnosis, prognosis, survivability, treatment, etc. of the individual.

A clinical pathology laboratory may use such techniques to determine regions of interest such as tumors, as well as tumor classes of tumor samples, and/or to compare or validate determinations of tumor classes by individuals and/or other automated processes. A researcher may use such techniques to determine tumor classes of tumors in images of a research data set, which may be from human patients or from human or non-human experimental subjects, where such research may involve further techniques for classifying tumors, determining the prevalence and classes of tumors in different demographics, determining risk factors that are correlated with tumors of different tumor classes, projecting survivability, for determining or comparing the effectiveness of treatment options. A clinician may use the results of the classification to evaluate the diagnostic, prognostic, and/or treatment options for an individual with a tumor, and/or to explore and understand the correlation of various risk factors with different tumor classes and the prognoses of individuals with such tumors In some example embodiments, the training data set 100 may include images 102, region of interest labels 604, and/or annotation masks 610 prepared by a human labeler, such as a pathologist or a clinician. Alternatively or additionally, the training data set 100 may include images 102, region of interest labels 604, and/or annotation masks 610 selected from a reference source, such as The Cancer Genome Atlas Project. Alternatively or additionally, the training data set 100 may include images 102, region of interest labels 604, and/or annotation masks 610 generated by an automated process, such as an automated tissue staining and preparation system, and/or by another machine learning model. As another such example, the training data set 100 may include images 102, region of interest labels 604, and/or annotation masks 610 generated by a specialized machine learning model that has been trained to recognize a specific type of tumor, wherein the classifier 600 may be trained to generalize the determinations of the specialized machine learning model to recognize a wider set of types of tumors. In some example embodiments, the training data set 100 may include images 102 of a single type, such as images 102 of tissues of one type of tumor and/or prepared using one type of preparation technique, such as one stain or dye. In other example embodiments, the training data set 100 may include images 102 of multiple types, such as images 102 of tissues of multiple types of tumor and/or prepared using a variety of types of preparation techniques such as different stains or dyes. In still other example embodiments, the training data set 100 may include images 102 of one type of tissue or region of interest 702 at different stages, such as tumors of one type but at different stages of development, and/or that have been subjected to different stages of treatment, such as pre-treatment tumors and post-treatment tumors, and/or that have been subjected to different treatments, such as different types of cancer therapeutics.

I2. Machine Learning Models for Region of Interest Classifier

In some example embodiments, machine learning models, including deep learning models, may be used for the detection of various features of various inputs. In various example embodiments, such machine learning models may be used to determine the feature map 118 of an image 102, for example, by generating and applying a mask set 300 of masks 302; to determine a distribution of the features, such as clusters 204; to perform a classification of areas of an image, such as area types based on anatomic features and/or tissue types; to perform a measurement 304 of a feature, such as a concentration (e.g., percentage area of an entire image) of a feature or an area type, for example, a lymphocyte density range estimation 404, using techniques such as binning; to generate a density map, such as a lymphocyte density map 406; to choose a set of features to be used to classify images 102 or a particular image 102, such as performing a selection process to select a feature subset; to classify an image 102 of a tumor based on an image feature set or image feature subset; to select a clinical feature subset from a the values of clinical features of a clinical feature set for an individual or a tumor; to determine the values of clinical features of a clinical feature set for an individual and/or a tumor; to determine a class of a tumor, such as by preparing and applying a Cox proportional hazards model to clinical features of the tumor; to determine a class of a tumor based on image features of the tumor (such as the output of a Gaussian mixture model) and/or clinical features of the tumor or the individual (such as the output of a Cox proportional hazards model); to project a survivability for an individual based on a classification of a tumor of the individual; and/or to generate one or more outputs, including visualizations, of such determinations. Each of these features and other features of some example embodiments may be performed, for example, by a machine learning model; by a plurality of machine learning models of a same or similar type, such as random forests, or convolutional neural networks that evaluate different parts of an image or that perform different tasks on an image; and/or by a combination of machine learning models of different types. As one such example, in a boosting ensemble, a first machine learning model performs classification based on the output of other machine learning models.

As a first such example, the presence of the feature (e.g., an activation within a feature map, and/or a biological activation of lymphocytes) may be determined in various ways. For example, where an input further includes an image 102, the determining of the presence of the feature may be performed by applying at least one convolutional neural network 110 to the image 102 and receiving, from the at least one convolution neural network 110, a feature map 118 indicating the presence of the feature of the input. That is, a convolutional neural network 110 may be applied to an image 102 to determine clusters of pixels 108 in which a feature is apparent. For example, cell-counting convolutional neural networks 110 may be applied to count cells in a tissue sample, where such cells may be lymphocytes. In such scenarios, the tissue sample may be subjected to an assay, such as a dye or a luminescent (such as fluorescent) agent, and a collection of images 102 of the tissue sample may be selective for the cells and may therefore not include other visible components of the tissue sample. The image 102 of the tissue sample may then be subjected to a machine learning model (such as a convolutional neural network 110) that may be configured (e.g., trained) to detect shapes such as circles that are indicative of the selected cells, and may output a count in the image 102 and/or for different areas of the image 102. Notably, the convolutional neural network 110 in this case may not be configured and/or used to further detect an arrangement of such features, for example, a number, orientation, and/or positioning of lymphocytes with respect to other lymphocytes; rather, the counts of respective portions of the image 102 may be compiled into a distribution map that may be processed together with a tumor mask to determine the distribution of lymphocytes as being tumor-invasive, tumor-adjacent, or elsewhere in the tissue sample. Some example embodiments may use a machine learning model other than a convolutional neural network to detect the presence of a feature, such as (e.g.) a non-convolutional neural network such as a fully-connected network or a perceptron network or a Bayesian classifier.

As a second such example, a distribution of the feature may be determined in a variety of ways. As a first example, where the input further includes an image 102 illustrating a tissue region of an individual, determining the distribution of the feature further may include determining an area type (e.g., tumor or non-tumor) for each area of the image, and determining the distribution based on the area type of each area of the image. The distribution of detected lymphocytes, including lymphocyte counts, may then be determined based upon the types of tissue in which such counts occur. That is, the distribution may be determined by tabulating counts of lymphocytes for tumor areas, tumor-adjacent areas (such as stroma), and non-tumor areas of the image 102. As another such example, the determining may include determining a boundary of the tissue region within the image 102, and determining the distribution based on the boundary of the tissue region within the image 102. That is, the boundaries of the areas of the image 102 that are classified as tumor may be determined (e.g., by a convolutional neural network 110 and/or a human), and an example embodiment may tabulate the counts of lymphocytes for all of the areas of the image that are within the determined boundaries of the tumor. As yet another example, the tissue region of the image including at least two areas, and determining the distribution may include determining a count of lymphocytes within each area of the tissue region and determining the distribution based on the count within each area of the tissue region. For example, determining the count within each tissue region may include determining a density of the count of lymphocytes within each area, and then determining the distribution based on the count within each area. An example is shown in FIG. 3, in which a first convolutional neural network 110-1 is provided to classify areas as tumor vs. non-tumor areas and a second convolutional neural network 110-2 is provided to estimate a density range of lymphocytes.

As a third such example, the processing of an image 102 to determine the presence of a feature and/or the distribution of a feature may occur in several ways. For example, some example embodiments may be configured to partition an image 102 into a set of areas of the same or varying sizes and/or shapes, such as based on a number of pixels or a corresponding physical size (e.g., 100 µm$^2$ areas), and/or based on similarity grouping (e.g., determining areas of similar appearance within the image 102). Some example embodiments may be configured to classify each area (for example, as tumor, tumor-adjacent, or non-tumor), and/or to determine the distribution by tabulating the presence of the feature (e.g., a count) within each area of a certain area type to determine the distribution of lymphocytes. Alternatively, a counting process may be applied to each area, and each area may be classified based on a count (e.g., high-lymphocyte vs. low-lymphocyte areas). As yet another example, the distributions may be determined in a parametric manner, such as according to a selected distribution type or kernel that a machine learning model may fit to the distribution of the feature in the input (e.g., a Gaussian mixture model may be applied to determine Gaussian distributions of subsets of the feature). Other distribution models may be applied, including parametric distribution models such as chi-square fit, a Poisson distribution, and a beta distribution and non-parametric distribution models such as histograms, binning, and kernel methods. It may be appreciated by persons of ordinary skill in the art that each type of distribution may have different distribution features (e.g., mean, deviation, higher order moments, etc.), which may be used within the classifiers.

As a fourth such example, a classifier 600 trained to determine a region of interest 702 may be a convolutional neural network 110 featuring one or more convolutional layers, such as shown in FIG. 1, wherein a first convolutional layer 112-1 receives an image 102 and generates a first feature map 118-1 based on a first set of convolutional filters, and a second convolutional layer 112-2 receives the first feature map 118-2 and generates a second feature map 118-2 based on a second set of convolutional filters, etc. Such a classifier 600 may include a classification layer 608, such as a convolutional classification layer 120 that receives a last feature map 118-3 and performs a classification 122 of a region of interest 702 based on the last feature map 118-3. One such convolutional neural network 110 is an Inception v3 convolutional model, but other models of convolutional neural networks 110 may be trained as a classifier 600 in accordance with the techniques presented herein. Examples of convolutional neural network classifiers include, without limitation, LeNet, ZfNet, AlexNet, BN-Inception, CaffeResNet-101, DenseNet-121, DenseNet-169, DenseNet-201, DenseNet-161, DPN-68, DPN-98, DPN-131, FBResNet-152, GoogLeNet, Inception-ResNet-v2, Inception-v3, Inception-v4, MobileNet-v1, MobileNet-v2, NASNet-A-Large, NASNet-A-Mobile, ResNet-101, ResNet-152, ResNet-18, ResNet-34, ResNet-50, ResNext-101, SE-ResNet-101, SE-ResNet-152, SE-ResNet-50, SE-ResNeXt-101, SE-ResNeXt-50, SENet-154, ShuffleNet, SqueezeNet-v1.0, SqueezeNet-v1.1, VGG-11, VGG-11_BN, VGG-13, VGG-13_BN, VGG-16, VGG-16_BN, VGG-19, VGG-19_BN, Xception, DelugeNet, FractalNet, WideResNet, PolyNet, PyramidalNet, and U-net.

Further, non-convolutional machine learning models may be trained as a classifier 600 in accordance with the techniques presented herein, as well as combinations thereof. Examples of other machine learning models that may be trained as a classifier 600 in accordance with the techniques presented herein include Bayesian (including naïve Bayesian) classifiers; Gaussian classifiers; probabilistic classifiers; principal component analysis (PCA) classifiers; linear discriminant analysis (LDA) classifiers; quadratic discriminant analysis (QDA) classifiers; single-layer or multiplayer perceptron networks; convolutional neural networks; recurrent neural networks; nearest-neighbor classifiers; linear SVM classifiers; radial-basis-function kernel (RBF) SVM classifiers; Gaussian process classifiers; decision tree classifiers;

and/or restricted or unrestricted Boltzmann machines; sequential models; and attention-based models, among others. Still others may involve an ensemble of one or more machine learning models, such as two or more convolutional neural networks that operate in tandem (e.g., a Siamese network); a random forest of decision tree classifiers; and/or a combination of different machine learning models, such as a boosting model in which output from different classifiers 600 is used to determine a classification based on a consensus.

In some example embodiments, classification may include regression, and the term "classification" as used herein is intended to include some example embodiments that perform regression as an alternative to, or in addition to, a selection of a class. For example, some example embodiments may feature regression as an alternative to or additional to classification. As a first such example, a determination of a presence of a feature may include a regression of the presence of the feature, for example, a numerical value indicating a density of the feature in an input. As a second such example, a determination of a distribution of a feature may include a regression of the distribution of the feature, such as a variance of the regression-based density determined for the input. As a third such example, the choosing may include performing a regression of the distribution of the feature and choosing a regression value for the distribution of the feature. Such regression aspects may be performed instead of classification or in addition to a classification (for example, determining both a presence of the feature and a density of the feature in an area of an image). Some example embodiments may involve regression-based machine learning models, such as Bayesian linear or nonlinear regression, regression-based artificial neural networks such as convolutional neural network regression, support vector regression, and/or decision tree regression.

Each classifier may be linear or nonlinear; for example, a nonlinear classifier may be provided (e.g., trained) to perform a linear classification based upon a kernel transform in a nonlinear space, that is, a transformation of linear values of a feature vector into nonlinear features. The classifiers may include a variety of techniques to promote accurate generalization and classification, such as input normalization, weight regularization, and/or output processing, such as a softmax activation output. The classifiers may use a variety of techniques to promote efficient training and/or classification. For example, a two-way Gaussian mixture model may be used in which a same size of the Gaussian distributions is selected for each dimension of the feature space, which may reduce the search space as compared with other Gaussian mixture models in which the sizes of the distribution for different dimensions of the feature space may vary.

Each classifier may be trained to perform classification in a particular manner, such as supervised learning, unsupervised learning, and/or reinforcement learning. Some example embodiments may include additional training techniques to promote generalization, accuracy, and/or convergence, such as validation, training data augmentation, and/or dropout regularization. Ensembles of such classifiers may also be utilized, where such ensembles may be homogeneous or heterogeneous, and wherein the classification 122 based on the outputs of the classifiers may be produced in various ways, such as by consensus, based on the confidence of each output (e.g., as a weighted combination), and/or via a stacking architecture such as based on one or more blenders. The ensembles may be trained independently (e.g., a bootstrap aggregation training model, or a random forest training model) and/or in sequence (e.g., a boosting training model, such as Adaboost). As an example of a boosting training model, in some support vector machine ensembles, at least some of the support vector machines may be trained based on an error of a previously trained support vector machine; e.g., each successive support vector machine may be trained particularly upon the inputs of the training data set 100 that were incorrectly classified by previously trained support vector machines.

As a fifth such example, various forms of classification 122 may be produced by the one or more classifiers. For example, a perceptron or binary classifier may output a value indicating whether an input is classified as a first class 106 or a second class 106, such as whether an area of an image 102 is a tumor area or a non-tumor area. As another example, a probabilistic classifier may be configured to output a probability that the input is classified into each class 106 of the class set 104. Alternatively or additionally, some example embodiments may be configured to determine a probability of classifying the input into each class 106 of the class set 104, and to choose, from a class set 104 including at least two classes 106, a class 106 of the input, the choosing being based on probabilities of classifying the input into each class 106 of the class set 104. For example, a classifier may output a confidence of the classification 122, e.g., a probability of classification error, and/or may refrain from outputting a classification 122 based upon poor confidence, e.g., a minimum-risk classifier. For example, in areas of an image 102 that are not clearly identifiable as tumor or non-tumor, a classifier may be configured to refrain from classifying the area in order to promote accuracy in the calculated distribution of lymphocytes in areas that may be identified as tumor and non-tumor with acceptable confidence.

As a sixth such example, some example embodiments may be configured to process the distribution of a feature with a linear or nonlinear classifier, and may receive, from the linear or nonlinear classifier, a classification 122 of the class 106 of the input. For example, a linear or nonlinear classifier may include a support vector machine ensemble of at least two support vector machines, and some example embodiments may be configured to receive the classification 122 by receiving, from each of the at least two support vector machines, a candidate classification 122, and to determine the classification 122 based on a consensus of the candidate classifications 122 among the at least two support vector machines.

As a seventh such example, some example embodiments may be configured to use a linear or nonlinear classifier (including a set or ensemble of classifiers) to perform a classification 122 of an input in a variety of ways. For example, an input may be partitioned into areas, and for each input portion, an example embodiment may use a classifier to classify the input portion according to an input portion type selected from a set of input portion types (e.g., performing a classification 122 of portions of an image 102 of a tumor as tumor areas vs. non-tumor areas, such as shown in the example of FIG. 3). The example embodiment may then be configured to choose, from a class set including at least two classes, a class of the input, the choosing based on the distribution of the feature for each input portion of an input portion type and the distribution of the feature for each input portion type of the set of input portion types (e.g., classifying areas of tumor-invasive lymphocytes (TIL), tumor-adjacent lymphocytes such as in stroma, high-activation lymphocyte areas, and/or low-activation lymphocyte areas).

As an eighth such example, some example embodiments may be configured to perform a distribution classification by determining a variance of the distribution of the feature of the input, e.g., the variance of the distribution over the areas of an input such as an image 102. Some example embodiments may then be configured to perform classification 122 by choosing, from a class set 104 including at least two classes 106, a class 106 of the input, the choosing being based on the variance of the distribution of the feature of the input and the variance of distribution of the feature for each class 106 of the class set 104. For example, some example embodiments may be configured to determine a class of a tumor based, at least in part, upon the variance of the distribution of lymphocytes over the different areas of the image.

As a ninth such example, some example embodiments may use different training and/or testing to generate and validate the machine learning models. For example, training may be performed using heuristics such as stochastic gradient descent, nonlinear conjugate gradient, or simulated annealing. Training may be performed offline (e.g., based on a fixed training data set 100) or online (e.g., continuous training with new training data). Training may be evaluated based on various metrics, such as perceptron error, Kullback-Leibler (KL) divergence, precision, and/or recall. Training may be performed for a fixed time (e.g., a selected number of epochs or generations), until training fails to yield additional improvement, and/or until reaching a point of convergence (for example, when classification accuracy reaches a target threshold). A machine learning model may be tested in various ways, such as k-fold cross-validation, to determine the proficiency of the machine learning model on previously unseen data. Many such forms of classification 122, classifiers, training, testing, and validation may be included and used in some example embodiments.

J. Example Computing Environment

Figure 14:
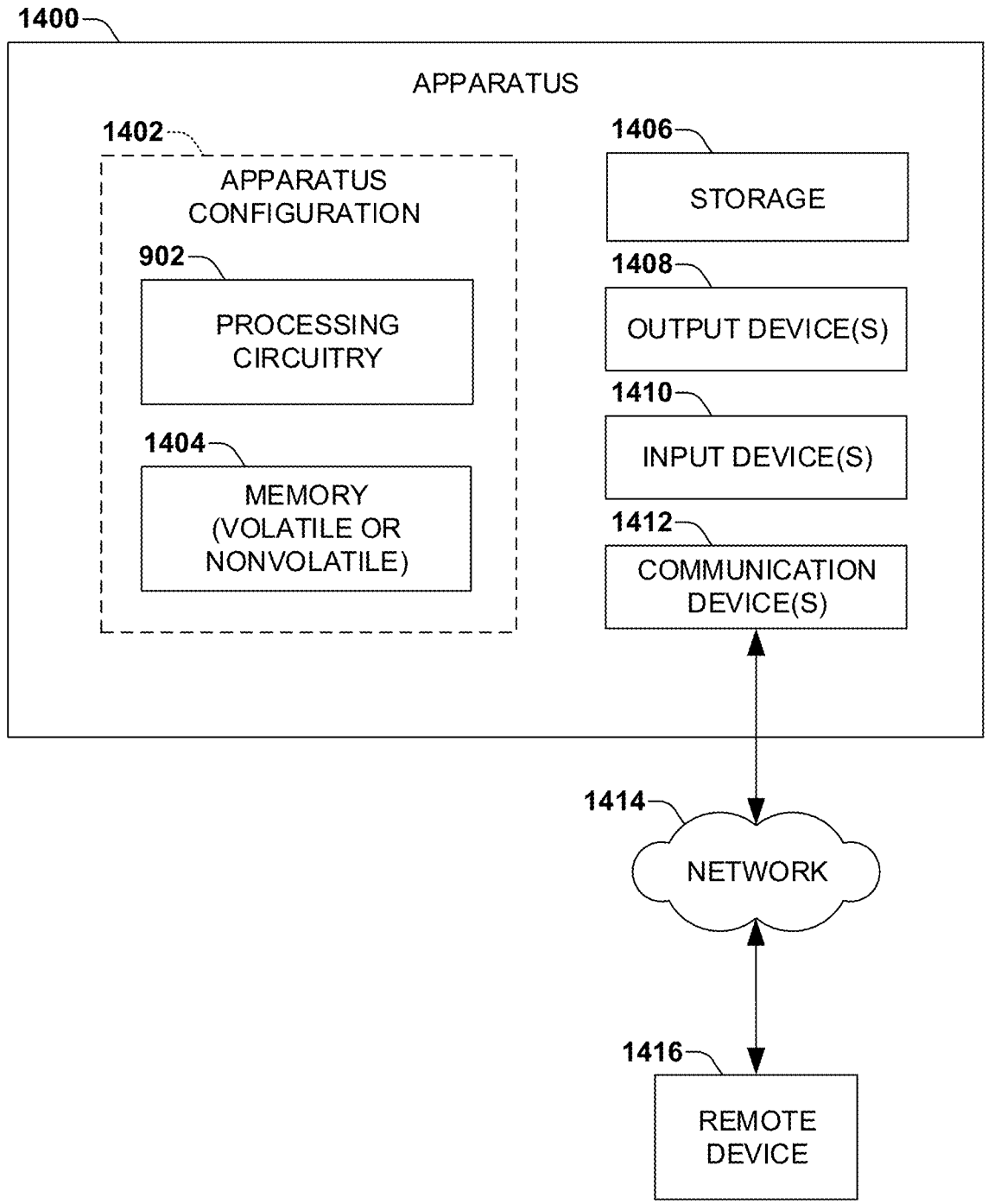
FIG. 14 is an illustration of an example apparatus in which some example embodiments may be implemented.

FIG. 14 is an illustration of an example apparatus in which some example embodiments may be implemented.

FIG. 14 and the following discussion provide a brief, general description of a suitable computing environment to implement embodiments of one or more of the provisions set forth herein. The operating environment of FIG. 14 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, media devices such as televisions, consumer electronics, embedded devices, mini computers, mainframe computers, distributed computing environments that include any of the above systems or devices, wearable computing devices (such as glasses, earpieces, wristwatches, rings, pendants, handheld and/or body-mounted cameras, clothing-integrated devices, and implantable devices), autonomous vehicles, extended reality (XR) devices such as augmented reality (AR) and/or virtual reality (VR) devices, internet-of-things (IoT) devices, and the like.

Some example embodiments may include a combination of components of the same and/or different types, such as a plurality of processors and/or processing cores in a uniprocessor or multi-processor computer; two or more processors operating in tandem, such as a CPU and a GPU; a CPU utilizing an ASIC; and/or software executed by processing circuitry. Some example embodiments may include components of a single device, such a computer including one or more CPUs that store, access, and manage the cache. Some example embodiments may include components of multiple devices, such as two or more devices having CPUs that communicate to access and/or manage a cache. Some example embodiments may include one or more components that are included in a server computing device, a server computer, a series of server computers, server farm, a cloud computer, a content platform, a mobile computing device, a smartphone, a tablet, or a set-top box. Some example embodiments may include components that communicate directly (e.g., two or more cores of a multi-core processor) and/or indirectly (e.g., via a bus, via over a wired or wireless channel or network, and/or via an intermediate component such as a microcontroller or arbiter). Some example embodiments may include multiple instances of systems or instances that are respectively performed by a device or component, where such systems instances may execute concurrently, consecutively, and/or in an interleaved manner. Some example embodiments may feature a distribution of an instance or system over two or more devices or components.

Although not required, some example embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 14 illustrates an example of an example apparatus 1400 configured as, or to include, one or more example embodiments, such as the example embodiments provided herein. In one apparatus configuration 1402, the example apparatus 1400 may include processing circuitry 902 and memory 1404. Depending on the exact configuration and type of computing device, memory 1404 may be volatile (such as RAM, for example), nonvolatile (such as ROM, flash memory, etc., for example) or some combination of the two.

In some example embodiments, an example apparatus 1400 may include additional features and/or functionality. For example, an example apparatus 1400 may also include additional storage (e.g., removable and/or non-removable) including, but not limited to, magnetic storage, optical storage, and the like. Such additional storage is illustrated in FIG. 14 by storage 1406. In some example embodiments, computer-readable instructions to implement one or more embodiments provided herein may be stored in the memory 1404 and/or the storage 1406.

In some example embodiments, the storage 1406 may be configured to store other computer readable instructions to implement an operating system, an application program, and the like. Computer-readable instructions may be loaded in memory 1404 for execution by processing circuitry 902, for example. Storage may include volatile and nonvolatile, removable and non-removable media implemented in any method or technology for storage of information such as computer readable instructions or other data. Storage may include, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which may be used to store the desired information and which can be accessed by example apparatus 1400. Any such computer storage media may be part of example apparatus 1400.

In some example embodiments, an example apparatus 1400 may include input device(s) 1410 such as keyboard, mouse, pen, voice input device, touch input device, infrared cameras, video input devices, and/or any other input device. Output device(s) 1408 such as one or more displays, speakers, printers, and/or any other output device may also be included in example apparatus 1400. Input device(s) 1410 and output device(s) 1408 may be connected to example apparatus 1400 via a wired connection, wireless connection, or any combination thereof. In some example embodiments, an input device or an output device from another computing device may be used as input device(s) 1410 or output device(s) 1408 for example apparatus 1400.

In some example embodiments, an example apparatus 1400 may be connected by various interconnects, such as a bus. Such interconnects may include a Peripheral Component Interconnect (PCI), such as PCI Express, a Universal Serial Bus (USB), Firewire (IEEE 1394), an optical bus structure, and the like. In other example embodiments, components of an example apparatus 1400 may be interconnected by a network. For example, memory 1404 may include multiple physical memory units located in different physical locations interconnected by a network.

In some example embodiments, an example apparatus 1400 may include one or more communication device(s) 1412 by which the example apparatus 1400 may communicate with other devices. Communication device(s) 1412 may include, for example, a modem, a Network Interface Card (NIC), an integrated network interface, a radio frequency transmitter/receiver, an infrared port, a USB connection, or other interfaces for connecting the example apparatus 1400 to other computing devices, including remote devices 1416. Communication device(s) 1412 may include a wired connection or a wireless connection. Communication device(s) 1412 may be configured to transmit and/or receive communication media.

Those skilled in the art will realize that storage devices used to store computer readable instructions may be distributed across a network. For example, an example apparatus 1400 may communicate with a remote device 1416 via a network 1414 to store and/or retrieve computer-readable instructions to implement one or more example embodiments provided herein. For example, an example apparatus 1400 may be configured to access a remote device 1416 to download a part or all of the computer-readable instructions for execution. Alternatively, an example apparatus 1400 may be configured to download portions of the computer-readable instructions as needed, wherein some instructions may be executed at or by the example apparatus 1400 and some other instructions may be executed at or by the remote device 1416.

In this application, including the definitions below, the term "module" or the term "controller" may be replaced with the term "circuit." The term "module" may refer to, be part of, or include processing circuitry 902 (shared, dedicated, or group) that executes code and memory hardware (shared, dedicated, or group) that stores code executed by the processing circuitry 902.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processing circuitry 902 may encompass a single microprocessor that executes some or all code from multiple modules. Group processing circuitry 902 may encompass a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The example embodiments of apparatuses and methods described herein may be partially or fully implemented by a special-purpose computer created by configuring a general-purpose computer to execute one or more particular functions embodied in computer programs. The functional blocks and flowchart elements described herein may serve as software specifications, which may be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

K. Use of Terms

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any other example embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "component," "module," "system," "interface," and the like are generally intended to refer to a computer-related entity, either hardware, a combination of hardware and software, software, or software in execution. For example, a component may be, but is not limited to being, a process running on processing circuitry 902, processing circuitry 902, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, some example embodiments may include a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Various operations of embodiments are provided herein. In some example embodiments, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each example embodiment provided herein.

As used herein, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. The articles "a" and "an" as used herein and in the appended claims may generally be construed to mean "one or more" unless specified otherwise or clear from context to be directed to a singular form.

Although the disclosure has been shown and described with respect to some example embodiments, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated some example embodiments of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. An apparatus comprising:
   processing circuitry configured to:
      partition an image of tissue of an individual into a set of areas,
      identify a tissue type of each area of the image,
      apply a classifier to the image to determine a region of interest, the classifier being configured to determine regions of interest based on the tissue types of the set of areas of the image,
      determine a spatial relationship between areas of a first tissue type and areas of a second tissue type, and
      present the image with an indicator of the spatial relationship.

2. A non-transitory computer-readable storage medium storing instructions that, when executed by processing circuitry, cause an apparatus to:
   partition an image of tissue of an individual into a set of areas,
   identify a tissue type of each area of the image,
   apply a classifier to the image to determine a region of interest, the classifier being configured to determine regions of interest based on the tissue types of the set of areas of the image,
   determine a spatial relationship between areas of a first tissue type and areas of a second tissue type, and
   present the image with an indicator of the spatial relationship.

3. A method of operating an apparatus including processing circuitry, the method comprising:
   executing, by the processing circuitry, instructions that cause the apparatus to:
      partition an image of tissue of an individual into a set of areas,
      identify a tissue type of each area of the image,
      apply a classifier to the image to determine a region of interest, the classifier being configured to determine regions of interest based on the tissue types of the set of areas of the image,
      determine a spatial relationship between areas of a first tissue type and areas of a second tissue type, and
      present the image with an indicator of the spatial relationship.

4. The method of claim 3, wherein the classifier is a convolutional neural network including a convolutional classification layer that has been trained to determine regions of interest in images based on the tissue types of the set of areas of the image.

5. The method of claim 3, wherein
   the instructions are further configured to store a description of the region of interest based on the tissue types of the set of areas; and
   the classifier is further configured to determine the region of interest by matching the description of the region of interest with the tissue types of the set of areas.

6. The method of claim 5, wherein the description of the region of interest includes one or more of:
   a number of a subset of areas of a tissue type,
   a size of a subset of areas of a tissue type,
   a density of a subset of areas of a tissue type,
   a moment of a subset of areas of a tissue type,
   a shape of a subset of areas of a tissue type,
   a symmetry of a subset of areas of a tissue type,
   a spatial distribution of a subset of areas of a tissue type,
   a visual appearance of a subset of areas of a tissue type, or
   a distance between a subset of areas of a first tissue type and a subset of areas of a second tissue type.

7. The method of claim 5, wherein the instructions further cause the apparatus to determine a similarity measurement between the region of interest in the image and the region of interest of the description.

8. The method of claim 5, wherein the instructions further cause the apparatus to generate the description based on a training data set of images of regions of interest.

9. The method of claim 8, wherein the instructions further cause the apparatus to:
   determine at least one area of at least one image of the training data set that does not match the description, and
   request information about the at least one area.

10. The method of claim 9, wherein the instructions further cause the apparatus to update the description based on receiving the information.

11. The method of claim 8, wherein generating the description includes:
    receiving, from a user, an indication of a region of interest in one or more of the images of the training data set, and
    generating the description based on features of the one or more images of the training data set and the indication received from the user.

12. The method of claim 11, wherein generating the description includes:
    partitioning an image of the training data set into a set of areas,
    determining the areas of the image of the training data set that are within the region of interest indicated by the user, and
    determining at least one visual feature of the areas of the image of the training data set that are within the region of interest indicated by the user.

13. The method of claim 5, wherein:
storing the description further includes:
- storing a first description of a tissue type of a first region type, and
- storing a second description of a tissue type of a second region type that is different than the first region type; and the classifier is further configured to:
- determine a first region of interest in the image by matching the set of areas of the image with the first description of the first region type, and
- determine a second region of interest in the image by matching the set of areas of the image with the second description of the second region type.

14. The method of claim 13, wherein:
the first description describes a cancerous tissue region type, and
the second description describes a noncancerous tissue region type.

15. The method of claim 13, wherein:
the first description describes a first cancer region type, and
the second description describes a second cancer region type that is different than the first cancer region type.

16. The method of claim 13, wherein the instructions further cause the apparatus to determine that a similarity measurement between the region of interest in the image and regions of interest of the first description is greater than a similarity measurement between the region of interest in the image and regions of interest of the second description.

17. The method of claim 3, wherein the instructions further cause the apparatus to:
generate at least one mask indicating the areas of one tissue type among the set of areas, and
present the image including the at least one mask.

18. The method of claim 17, wherein presenting the image includes one or both of:
presenting a first mask of a first tissue type with a first visual indicator, or
presenting a second mask of a second tissue type with a second visual indicator that is different than the first visual indicator.

19. The method of claim 3, wherein the instructions further cause the apparatus to present the image with an indicator of the set of areas of the image that are determined as the region of interest.

20. The method of claim 19, wherein:
the apparatus further stores a mask indicating a labeled region of interest, and
presenting the image includes presenting an indicator of the labeled region of interest.

21. The method of claim 3, wherein the instructions further cause the apparatus to generate at least one measurement of the region of interest based on at least one visual feature of the set of areas of the region of interest.

22. The method of claim 21, wherein the at least one measurement includes one or more of:
a size of the region of interest,
a shape of the region of interest,
a symmetry of the region of interest,
a color of the region of interest,
a density of the region of interest, or
a moment of the region of interest.

23. The method of claim 3, wherein the spatial relationship includes one or more of:
a union between the areas of the first tissue type and the areas of the second tissue type,
an intersection between the areas of the first tissue type and the areas of the second tissue type,
a complement between the areas of the first tissue type and the areas of the second tissue type, or
a distance between the areas of the first tissue type and the areas of the second tissue type.

24. The method of claim 3, wherein the instructions further cause the apparatus to determine a measurement of the spatial relationship between the areas of the first tissue type and the areas of the second tissue type.

25. The method of claim 3, wherein the instructions further cause the apparatus to determine one or more of:
a diagnosis of the individual based on the region of interest,
a prognosis of the individual based on the region of interest, or
a treatment of the individual based on the region of interest.

26. A method of operating an apparatus including processing circuitry, the method comprising:
executing, by the processing circuitry, instructions that cause the apparatus to:
store descriptions of regions of interest of images based on tissue types of sets of areas of the images,
generate descriptions of regions of interest based on a training data set of images of regions of interest, wherein generating the descriptions includes:
receiving, from a user, an indication of a region of interest in one or more of the images of the training data set, and
generating the descriptions based on features of the one or more images of the training data set and the indication received from the user,
partition an image of tissue of an individual into a set of areas,
identify a tissue type of each area of the image of tissue of the individual, and
apply a classifier to the image of tissue of the individual to determine a region of interest in the image of tissue of the individual, the classifier configured to determine the region of interest based on the tissue types of the set of areas of the image of tissue of the individual by matching a description of the region of interest with the tissue types of the set of areas of the image of tissue of the individual.

27. The method of claim 26, wherein generating the description includes:
partitioning an image of the training data set into a set of areas,
determining the areas of the image of the training data set that are within the region of interest indicated by the user, and
determining at least one visual feature of the areas of the image of the training data set that are within the region of interest indicated by the user.

28. The method of claim 26, wherein:
storing the description further includes:
storing a first description of a tissue type of a first region type, and
storing a second description of a tissue type of a second region type that is different than the first region type; and the classifier is further configured to:
determine a first region of interest in the image of tissue of the individual by matching the set of areas of the image of tissue of the individual with the first description of the first region type, and determine a second region of interest in the image of tissue of the individual by matching the set of areas of the image of tissue of the individual with the second description of the second region type.

29. The method of claim 28, wherein:

the first description describes a cancerous tissue region type, and the second description describes a noncancerous tissue region type.

30. The method of claim 28, wherein:

the first description describes a first cancer region type, and the second description describes a second cancer region type that is different than the first cancer region type.

* * * * *